(12) United States Patent
Harari et al.

(10) Patent No.: US 12,137,884 B2
(45) Date of Patent: Nov. 12, 2024

(54) SAMPLE COLLECTION DEVICES AND METHODS OF USING THE SAME

(71) Applicant: Harp Diagnostics Ltd., Misgav, IL (US)

(72) Inventors: Shahar Harari, Tel Aviv (IL); Avshalom Shenhav, Haifa (IL); Nir Goldenberg, Haifa (IL); Dotan Tromer, Moshav Hosen (IL); Arnon Hadas, Misgav (IL); Kobby Greenberg, Even Yehuda (IL)

(73) Assignee: Harp Diagnostics Ltd., Misgav (IL)

( * ) Notice: Subject to any disclaimer, the term of this patent is extended or adjusted under 35 U.S.C. 154(b) by 1031 days.

(21) Appl. No.: 17/084,424

(22) Filed: Oct. 29, 2020

(65) Prior Publication Data
US 2021/0128121 A1   May 6, 2021

Related U.S. Application Data

(60) Provisional application No. 62/929,195, filed on Nov. 1, 2019.

(51) Int. Cl.
| | | |
|---|---|---|
| *A61B 10/00* | (2006.01) | |
| *A61B 5/00* | (2006.01) | |
| *G01N 1/10* | (2006.01) | |
| *G01N 33/48* | (2006.01) | |
| *G01N 33/50* | (2006.01) | |

(52) U.S. Cl.
CPC ........ *A61B 10/0038* (2013.01); *A61B 5/7435* (2013.01)

(58) Field of Classification Search
CPC .. A61B 10/0038; A61B 5/7435; G01N 33/50; G01N 1/10; G01N 33/48
See application file for complete search history.

(56) References Cited

U.S. PATENT DOCUMENTS 2,528,976 A   11/1950   Schiavone
3,936,373 A    2/1976   Studer
(Continued)

FOREIGN PATENT DOCUMENTS

WO   2013025917 A1   2/2013

OTHER PUBLICATIONS

Buehlmann Laboratories AG. IBDoc Instructions for Use, Patients and Lay Users, Buehlmann, 2016. LF-IBDOC8, Version 3.3: Dec. 19, 2016 (32 pages, in English).
(Continued)

*Primary Examiner* — Rene T Towa
*Assistant Examiner* — Justin Xu
(74) *Attorney, Agent, or Firm* — The Roy Gross Law Firm, LLC; Roy Gross

(57) ABSTRACT

A sample collection device that includes a body having a proximal end and a distal end, the body defining a channel extending from the distal end to the proximal end. The sample collection device includes an opening at the proximal end of the body that extends into the channel of the body. The body includes an adhering portion having a depressed surface relative to an adjacent exterior surface of the body, the adhering portion configured to receive a sample in response to the sample contacting the depressed surface of the adhering portion. The body is manually maneuverable in response to the channel receiving a finger of a user through the opening of the body.

5 Claims, 14 Drawing Sheets

(56) References Cited

U.S. PATENT DOCUMENTS

| | | |
|---|---|---|
| 11,420,236 B2* | 8/2022 | Nonaka .................... B06B 3/00 |
| 2003/0206829 A1* | 11/2003 | Cui ........................ B01L 3/502 |
| | | 422/400 |
| 2011/0146420 A1* | 6/2011 | Okada .................. B01L 3/5021 |
| | | 73/864.51 |
| 2013/0118277 A1 | 5/2013 | Rodriguez |
| 2017/0215849 A1* | 8/2017 | Wei ..................... A61F 13/2005 |
| 2017/0269074 A1 | 9/2017 | Guirguis |
| 2018/0235582 A1* | 8/2018 | Dai .................... A61B 10/0038 |
| 2019/0049442 A1* | 2/2019 | Guirguis ............ A61B 10/0038 |
| 2022/0168740 A1* | 6/2022 | Lendvay ........... B01L 3/502761 |

OTHER PUBLICATIONS

International Search Report and Written Opinion in International Application No. PCT/US2020/058035, mailed Feb. 26, 2021 (14 pages).

* cited by examiner

SAMPLE COLLECTION DEVICES AND METHODS OF USING THE SAME

CROSS-REFERENCE TO RELATED APPLICATIONS

This application claims the benefit of priority from U.S. Provisional Application No. 62/929,195, filed on Nov. 1, 2019, which is incorporated by reference herein in its entirety.

TECHNICAL FIELD

Various aspects of the present disclosure relate generally to sample collection systems, devices, and related methods. More specifically, at least certain embodiments of the present disclosure relate to systems, devices, and related methods for collecting and analyzing stool samples, among other aspects.

BACKGROUND

Inflammatory bowel diseases (IBD), such as Crohn's disease (CD), ulcerative colitis (UC) and others, and/or various types of diarrhea, may generally be diagnosed by analyzing a stool sample in laboratory tests of blood and fecal matter. For example, stool specimens are analyzed to eliminate the possibility of bacterial, viral, or parasitic causes of diarrhea. Human calprotectin is generally a known marker in human feces specimens for IBD. Blood tests may check for signs of infection and anemia, which may indicate bleeding in the colon or rectum.

It is with these considerations in mind that a variety of advantageous medical outcomes may be realized by the devices, systems, and methods of the present disclosure.

SUMMARY

Aspects of the disclosure relate to, among other things, systems, devices, and methods for collecting a sample with a device, among other aspects. Each of the aspects disclosed herein may include one or more of the features described in connection with any of the other disclosed aspects.

According to an example, a sample collection device includes a body having a proximal end and a distal end, the body defining a channel extending from the distal end to the proximal end. The sample collection device includes an opening at the proximal end of the body that extends into the channel of the body. The body includes an adhering portion having a depressed surface relative to an adjacent exterior surface of the body, and the adhering portion configured to receive a sample in response to the sample contacting the depressed surface of the adhering portion. The body is manually maneuverable in response to the channel receiving a finger of a user through the opening of the body.

Any of the sample collection devices described herein may have any of the following features. The depressed surface of the adhering portion is at least one of a groove, a notch, a crevice, a cavity, a recess, or a slot. A size of the at least one groove, notch, crevice, cavity, recess, or slot of the adhering portion corresponds to a predetermined volume of the sample. The sample collection device may include a paper having an opening extending between an interior surface and an exterior surface of the paper, wherein the body is configured to selectively engage the interior surface of the paper. The adhering portion is alignable with the opening when the body engages the interior surface of the paper such that the adhering portion is exposed along the exterior surface of the paper through the opening of the paper. The paper is configured to collect excess quantities of the sample over the body, and at least a portion of the sample is receivable into the adhering portion through the opening of the paper. The paper is configured to at least partially remove excess quantities of the sample disposed over the body in response to disengaging the body from the paper. The sample collection device may include a sample test device including an opening sized to receive the body, wherein the sample test device includes a non-transitory computer readable medium storing instructions that, when executed by one or more processors, cause the one or more processors to test the sample in response to receiving the body through the opening of the sample test device. The sample test device includes at least one substance configured to detect a presence of a material within the sample when testing the sample. The at least one substance is one or more monoclonal antibodies, and the material within the sample is one or more IBD biomarkers and/or pathogens. The sample test device includes a seal disposed about the opening of the sample test device and configured to remove excess quantities of the sample from the adhering portion when the body is received within the sample test device through the opening of the sample test device. The sample test device includes a seal disposed about the opening of the sample test device and is configured to inhibit removal of the body from the opening of the sample test device when the finger of the user retracts from the sample test device. The sample test device includes an interface display, wherein the instructions stored on the non-transitory computer readable medium, when executed by the one or more processors, cause the one or more processors to display test results of the sample on the interface display. The sample collection device may include an outer boundary positioned along the body about the adhering portion, wherein the outer boundary defines an area for receiving the sample. Further including a docking station including an engagement platform, wherein the sample test device is coupled to the docking station along the engagement platform, and the sample is received from the sample test device and into the docking station via the engagement platform.

Any of the sample collection devices described herein may have any of the following features. The sample collection device may include a sample test device including an opening sized to receive the body, a collection device positioned adjacent to the opening and configured to extract the sample from the adhering portion, and a chamber sized to receive the sample from the collection device. The collection device is configured to move in a first direction within the chamber to contact the body and mix the sample extracted from the adhering portion with a substance stored in the chamber. The collection device is configured to move in a second direction within the chamber to deliver the mixture of the sample and the substance to a test apparatus disposed within the sample test device. The sample test device includes a non-transitory computer readable medium storing instructions that, when executed by one or more processors, cause the one or more processors to test the mixture of the sample and the substance in response to receiving the mixture from the collection device and onto the test apparatus. The test apparatus is configured to detect a presence of a material within the sample when testing the sample. The sample test device includes a motor operatively coupled to the collection device and configured to move the collection device in the first direction and the second direction in response to activation of the motor. The sample test device includes a sensing device positioned adjacent to the test apparatus within the sample test device and configured to capture images of the test apparatus. The sample test device includes an interface display, wherein the instructions stored on the non-transitory computer readable medium, when executed by the one or more processors, cause the one or more processors to display test results of the mixture of the sample and the substance on the interface display.

According to another example, a sample test device includes a housing including a first cavity, a second cavity, and a third cavity, at least one opening extending into the first cavity and configured to receive a sample device, a collection device movably disposed within the second cavity and configured to extend into the first cavity to contact the device, and a test apparatus disposed within the third cavity, the third cavity is in fluid communication with the second cavity, and the test apparatus is configured to obtain a sample received in the first cavity, via the sample device, in response to the collection device moving relative the second cavity.

Any of the sample test devices described herein may have any of the following features. The sample test device may include a movable receiver disposed within the first cavity, and a second opening positioned between the first cavity and the second cavity. The movable receiver is configured to close the second opening when in a first position, and to open the second opening when moved to a second position in response to the first cavity receiving the sample device via the at least one opening. The housing includes a channel extending between the second cavity and the third cavity. The collection device is configured to close the channel when in a first position relative to the second cavity, and to open the channel when moved to a second position relative to the second cavity. The sample test device includes a third opening extending into a fourth cavity of the housing and configured to receive a second sample device, wherein the second cavity is positioned between the first cavity and the fourth cavity, and the collection device is configured to extend into the fourth cavity to contact the second sample device.

According to another example, a sample collection assembly includes a platform, a pair of lateral supports extending outwardly from the platform, an aperture disposed through the platform, and a vessel including a bowl, a top lip extending about the bowl, and a sensor disposed within the bowl. The vessel is selectively attachable to the platform in response to engaging the top lip to the platform and receiving the bowl through the aperture such that the bowl is disposed below the platform. The vessel is configured to receive a sample within the bowl.

Any of the sample collection devices described herein may have any of the following features. The sample collection device may include a sealable carrier configured to enclose the vessel and inhibit contamination of the sample received within the bowl. The vessel includes an analysis module communicatively coupled to the sensor. The analysis module has a non-transitory computer readable medium storing instructions that, when executed by one or more processors, cause the one or more processors to test the sample within the bowl. The analysis module includes one or more monoclonal antibodies configured to detect a presence of one or more IBD biomarkers and/or pathogens within the sample when testing the sample. The pair of lateral supports are configured to engage a toilet having an opening such that the vessel is suspended over the opening when attached to the platform.

According to another example, a sample collection system includes a sample collection device, including a body having a proximal end, a distal end, and a channel extending from the distal end to the proximal end. The channel is sized to receive a finger of a user through an opening at the proximal end. The sample collection device includes an adhering portion on the body and including a plurality of grooves. The adhering portion is configured to receive a sample within at least one of the plurality of grooves in response to the sample contacting the adhering portion. The sample collection system includes a sample test device, including an opening sized to receive the body and a non-transitory readable medium storing instructions that, when executed by one or more processors, cause the one or more processors to test the sample in response to receiving the body through the opening of the sample test device.

Any of the sample collection systems described herein may have any of the following features. The sample collection system includes a sample test device, including an opening sized to receive the body, a collection device positioned adjacent to the opening and configured to contact the adhering portion to extract the sample from the at least one of the plurality of grooves, and a test apparatus configured to receive the sample from the collection device and test the sample for one or more characteristics.

According to another example, the embodiments disclosed herein provide improved devices and methods for collecting stool samples in a convenient and hygienic manner, as is described more in detail herein. There is thus provided in accordance with an embodiment of this disclosure a stool sample collection device including a thimble that includes a stool adhering portion to which fecal matter can adhere, an outer boundary of the stool adhering portion defining an area in which the stool adheres to the thimble. In accordance with an embodiment of the disclosure, the stool adhering portion includes slots or other crevices or cavities. The cavities become filled with fecal matter when the user wipes himself/herself after defecating. In normal use, the volume of fecal matter found on the stool sample collection device after wiping the rectal area is greater than the volume defined by the stool adhering portion, which is the volume needed for proper analysis of the stool sample. The excess fecal matter, that is, the amount that exceeds the required analytic volume, is removed upon inserting the thimble into the stool sample test device. Thus, even though wiping with the stool sample collection device provides an excessive stool collection amount, the amount of stool left in the stool adhering portion after insertion into the stool sample test device is sufficient for reliable and accurate stool analysis. In accordance with an embodiment of the disclosure, toilet paper may be placed over the thimble, the toilet paper being formed with a window through which the stool adhering portion is exposed. In accordance with an embodiment of the disclosure, a stool sample test device includes a stool analysis module for analyzing a stool sample adhered to the stool adhering portion. In accordance with an embodiment of the disclosure, the stool sample test device is formed with an opening sized to capture the thimble when placed in the opening and to allow a person to a finger on which the thimble is placed while the thimble remains in the test device. There is provided in accordance with another embodiment of the disclosure, stool sample collection device including a toilet platform configured to rest on a toilet bowl seat, the toilet platform being formed with an aperture, a stool collector vessel including a bowl portion for depositing therein a stool sample, and a sealable bag arranged to envelop the bowl portion. The bowl portion may be positioned above a stool analysis module. In accordance with an embodiment of the disclosure, the bowl portion is rigid. In accordance with another embodiment of the disclosure, the bowl portion is flexible and foldable.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
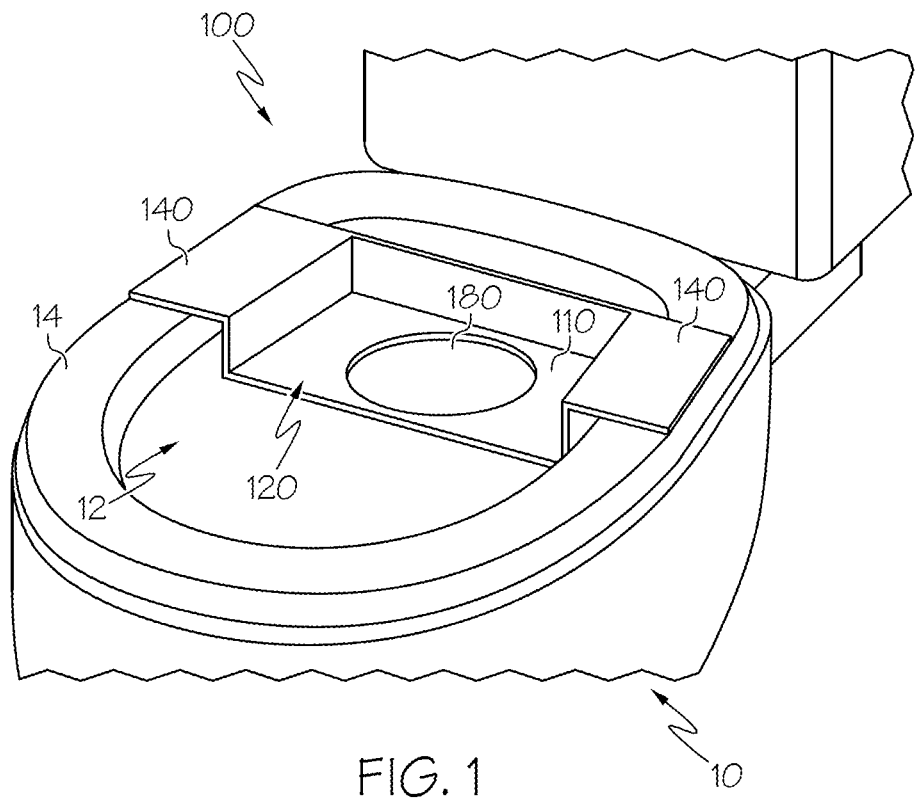
FIG. 1 is a perspective view of an exemplary sample collection device assembled onto a toilet seat, according to aspects of this disclosure.

The disclosure is drawn to systems, devices, and methods for collecting stool samples from a patient, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when handling a device. By contrast, the term "proximal" refers to a portion closest to the user when handling the device. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Collection of a stool sample may be accomplished by evacuating feces onto a device within a toilet below a patient's posterior. Use of such devices, however, may be unpleasant, unhygienic, or intrusive. Some devices may further compromise a sterility of a stool sample, which may become contaminated by urine or other materials present within the toilet bowl. Embodiments of the disclosure may provide a device that may address one or more of these concerns or other concerns and may be used to collect a material for testing and/or analyzing, such as, for example, stool samples that may comprise fecal matter, blood, etc. For example, a stool sample from a patient may be collected with a sample collection device of the disclosure that includes a platform and vessel positioned therein for receiving the stool sample. By way of further example, the sample collection device of the disclosure may analyze and/or test the fecal matter contained within the stool sample with an analysis module of the vessel. Embodiments of the disclosure may test for various diseases, including inflammatory bowel diseases such as Crohn's disease, and ulcerative colitis, and various types of diarrhea.

In one embodiment, a sample collection device may include an elongated housing (e.g., a thimble) that includes an adhering portion to which a material may adhere to, such as, for example, a sample of fecal matter. The adhering portion of the sample collection device may further include an outer boundary that defines a surface area in which the material may adhere onto the elongated housing. Various embodiments described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 2:
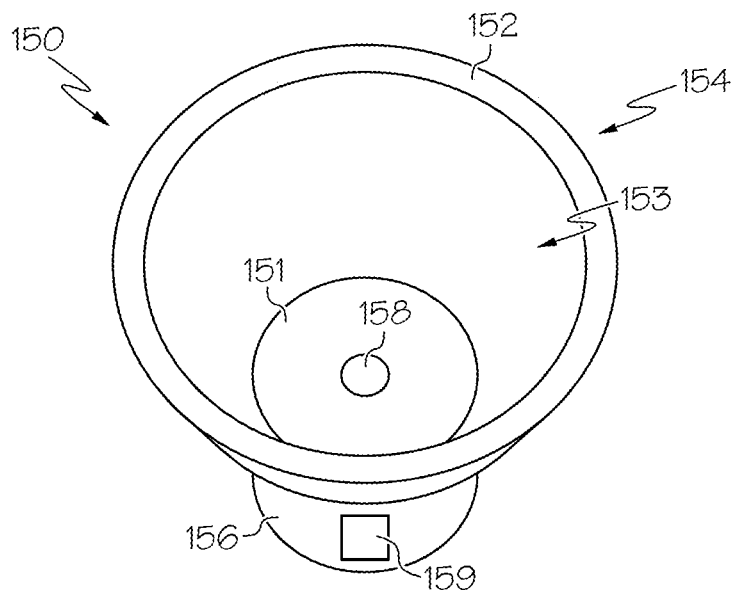
FIG. 2 is a perspective view of an exemplary vessel, according to aspects of this disclosure.

FIGS. 1-2 shows a perspective view of an exemplary sample collection device 100 in accordance with an embodiment of this disclosure. As seen in FIG. 1, the sample collection device 100 may include a toilet platform 120 and one or more lateral supports 140 that extend outward from the toilet platform 120. In the embodiment, the sample collection device 100 includes a pair of lateral supports 140 extending laterally outward at opposing ends of the toilet platform 120. Accordingly, the pair of lateral supports 140 are disposed about the toilet platform 120 such that the toilet platform 120 is positioned between the lateral supports 140. In the embodiment, the pair of lateral supports 140 are integral with the toilet platform 120 such that the lateral supports 140 form a unitary structure with the toilet platform 120, however, it should be understood that in other embodiments the one or more lateral supports 140 may be separate components secured and/or coupled to the toilet platform 120.

It should be appreciated that in other embodiments the sample collection device 100 may include additional and/or fewer lateral supports 140 than those shown and described herein without departing from a scope of this disclosure. The pair of lateral supports 140 extend relatively above a planar surface defined by the toilet platform 120, such that the pair of lateral supports 140 extends along a different plane than a planar surface of the toilet platform 120. The toilet platform 120 of the sample collection device 100 may include an aperture 180 disposed along the planar surface of the toilet platform 120. In this instance, the aperture 180 is positioned between the pair of lateral supports 140 and extends along a plane relatively below the pair of lateral supports 140. As described in greater detail herein, the aperture 180 of the toilet platform 120 is sized and shaped to receive one or more other components of the sample collection device 100 therein, such as, for example, a collector vessel 150 (FIG. 2).

Still referring to FIG. 1, the sample collection device 100 may be configured to removably couple to a structure, such as, for example, a toilet 10. In embodiments, the pair of lateral supports 140 of the sample collection device 100 may be sized, shaped, and configured to engage a seating surface 14 of the toilet 10. In embodiments, the lateral supports 140 may be configured to engage directly with the toilet 10 in addition to and/or in lieu of the seating surface 14, such as, for example, along a rim of the toilet 10. In this instance, the sample collection device 100 may rest on the toilet 10 as the pair of lateral supports 140 engage the seating surface 14. With the toilet platform 120 extending along a plane that is relatively below the pair of lateral supports 140, the planar surface of the toilet platform 120 may be disposed within an opening 12 of the toilet 10 when the pair of lateral supports 140 engage the seating surface 14. Accordingly, it should be understood that a lateral width of the toilet platform 120 may be sized in accordance with a size (e.g., width, diameter, etc.) of the opening 12 of the toilet 10.

As seen in FIG. 2, the sample collection device 100 may further include a collector vessel 150 which may include a bottom surface 151, a top lip 152, and a bowl portion 154. The bottom surface 151, the top lip 152, and/or the bowl portion 154 may collectively define a cavity 153 of the collector vessel 150. The cavity 153 is exposed along an end adjacent to the top lip 152 furthest from the bottom surface 151. As described in greater detail herein, the cavity 153 of the collector vessel 150 may be sized and shaped to receive one or more materials therein, such as, for example, a stool sample from a patient. In some embodiments, the bowl portion 154 may be formed of a rigid material (e.g., plastic, metal, etc.) such that a shape, size, and/or configuration of the bowl portion 154, and the cavity 153 partially formed by the bowl portion 154, is relatively static and/or fixed. Whereas in other embodiments, the bowl portion 154 may be formed of a flexible material (e.g., elastomer, plastic, etc.) such that a shape, size, and/or configuration of the bowl portion 154, and the cavity 153 partially formed by the bowl portion 154, is relatively deformable, sealable, and/or foldable.

In the embodiment, each of the bottom surface 151, the top lip 152, and the bowl portion 154 has a circular profile with varying diameters relative to one another. In embodiments, the bowl portion 154 is tapered and includes diameters that are relatively greater than that of the bottom surface 151, and relatively smaller than the top lip 152. Accordingly, as described in greater detail herein, the collector vessel 150 is configured to be received within the aperture 180 of the toilet platform 120. The bottom surface 151 and the bowl portion 154 are sized and shaped to be received through the aperture 180 and the top lip 152 is sized and shaped to engage a planar surface of the toilet platform 120, thereby securing the collector vessel 150 to the toilet platform 120. It should be understood that various suitable sizes, shapes, and/or configurations of the bottom surface 151, the top lip 152, and/or the bowl portion 154 may be included on the collector vessel 150 without departing from a scope of this disclosure. For example, the collector vessel 150 may be substantially cylindrical, conical, or pyramidal, for engagement with the toilet platform 120.

Still referring to FIG. 2, the collector vessel 150 may further include an analysis module 156 positioned relatively below the bowl portion 154. In this instance, the bottom surface 151 of the collector vessel 150 is positioned between the analysis module 156 and the bowl portion 154. In some embodiments, the analysis module 156 is a computer system that may include a non-transitory computer readable medium and one or more processors, memory, transceivers, and/or light emitting diodes (LEDs). The processor of the analysis module 156 may include any computing device capable of executing machine-readable instructions, which may be stored on a non-transitory computer-readable medium of the analysis module 156, such as, for example, a memory. By way of example, the processor may include a controller, an integrated circuit, a microchip, a computer, and/or any other computer processing unit operable to perform calculations and logic operations required to execute a program. The memory of the analysis module 156 may include any type of computer readable medium suitable for storing data and algorithms, such as, for example, random access memory (RAM), read only memory (ROM), a flash memory, a hard drive, and/or any device capable of storing machine-readable instructions.

The non-transitory computer readable medium of the analysis module 156 may store instructions that, when executed by the one or more processors of the analysis module 156, cause the one or more processors to perform certain operations. For example, the analysis module 156 may be configured to perform operations including analyzing a material received within the bowl portion 154 of the collector vessel 150. It should be understood that various programming algorithms and data that support an operation of the analysis module 156 may reside in whole or in part in the memory of the analysis module 156. In some embodiments, the analysis module 156 may be further configured to perform operations including generating a visual output of results from the analysis of material received within the bowl portion 154 on an interface display, such as, for example, a display 159 of the collector vessel 150 (see FIG. 4).

The bottom surface 151 of the collector vessel 150 may include a sampling element 158 (e.g. a sensor) disposed thereon that is communicatively coupled to the analysis module 156. In this instance, the sampling element 158 may be configured and operable to detect one or more properties, characteristics, and/or substances contained within a material (e.g., stool sample) in response to contacting the material within the cavity 153 of the bowl portion 154. A plurality of sensors may be included for detection of any of a variety of properties, characteristics, and/or substances in the collected sample. In some embodiments, the analysis module 156 may include the display 159 (see FIG. 4) positioned along an exterior surface of the analysis module 156 that is operable to display test results of the analysis executed by the analysis module 156. In other embodiments, the analysis module 156 may be operable to wirelessly communicate test results to a remote station (not shown), such as, for example, a mobile device, a computer, and/or the like.

In some embodiments, the analysis module 156 may store one or more substances therein for analyzing a material (e.g., stool sample) for the presence of predetermined bacteria, such as, for example, biomarkers and/or pathogens indicative of Inflammatory Bowel Disease (IBD), Crohn's Disease (CD), Ulcerative Colitis (UC), etc. For example, the one or more substances stored in the analysis module 156 may include monoclonal antibodies operable to determine a qualitative immunoassay for detection of human calprotectin in a material, such as stool samples of fecal matter. In embodiments, the analysis module 156 may include substances that are operable to detect the presence of fecal calprotectin within a stool sample, which may be indicative of Inflammatory Bowel Disease (IBD). By way of further example, suitable monoclonal antibodies that may be suitable in the analysis module 156 may include those disclosed in U.S. Patent Application Publication No. 2014/0227725, entitled "Competitive S100A9 Immunoassays," filed on Jun. 21, 2012, the entirety of which is incorporated herein by reference.

In embodiments, the material (e.g., stool sample) received within the collector vessel 150 may contact and/or interact with the one or more substances of the analysis module 156 for testing the material for a presence of the predetermined bacteria detailed above. In this instance, it should be appreciated that at least the collector vessel 150 of the stool sample collection device 100 may be configured for single-use such that a user of the sample collection device 100 may dispose of the collector vessel 150 after analyzing a single specimen (e.g., stool sample) with the analysis module 156. In other embodiments, the collector vessel 150 may be configured for multiple uses, e.g. for analyzing two or more specimens. By way of example, the collector vessel 150 may be configured such that the analysis module 156 of may be decoupled from the bottom surface 151 of the bowl portion 154 and additional analysis modules 156 may be selectively attached thereto for analysis of additional samples with the collector vessel 150. By way of further example, the one or more substances of the analysis module 156 may be selectively replaceable and/or at least partially shielded from contamination by the material (e.g., stool sample) received therein such that the analysis module 156 may be configured for multiple uses, e.g. for analyzing two or more specimens.

Figure 3A:
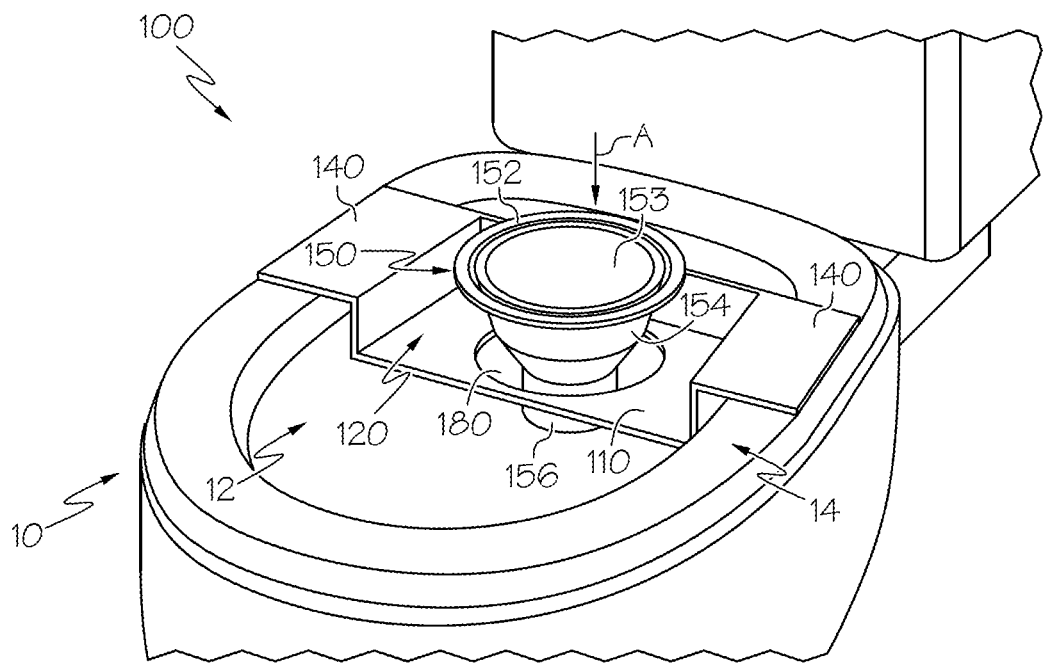
FIG. 3A is a perspective view of the vessel of FIG. 2 assembled onto the sample collection device of FIG. 1, according to aspects of this disclosure.

According to an example method of using the sample collection device 100, the sample collection device 100 may be coupled to the toilet 10 with the pair of lateral supports 140 engaged with the seating surface 14, as seen in FIG. 3A. In this instance, the toilet platform 120 may be at least partially disposed within the opening 12 of the toilet 10. In some embodiments, the lateral supports 140 may be substantially flush with the seating surface 14 when the sample collection device 100 is coupled to the toilet 10. In some embodiments, the lateral supports 140 may include additional supports for securing the toilet platform 120 around an edge of the seating surface 14 and/or a rim of the toilet 10. The collector vessel 150 is receivable within the opening 180 of the toilet platform 120 such that the collector vessel 150 is at least partially disposed within the opening 12 of the toilet 10. The collector vessel 150 is removably coupled to the toilet platform 120 in response to moving the collector vessel 150 in direction A until the top lip 152 engages a planar surface of the toilet platform 120. In this instance, the collector vessel 150 is suspended within the opening 12 of the toilet 10. It should be appreciated that with a planar surface of the toilet platform 120 positioned relatively below the lateral supports 140, and the lateral supports 140 engaged against the seating surface 14 of the toilet 10, the collector vessel 150 is maintained relatively below the seating surface 14 of the toilet 10 along a plane that is substantially parallel with a planar surface of the toilet platform 120.

Figure 3B:
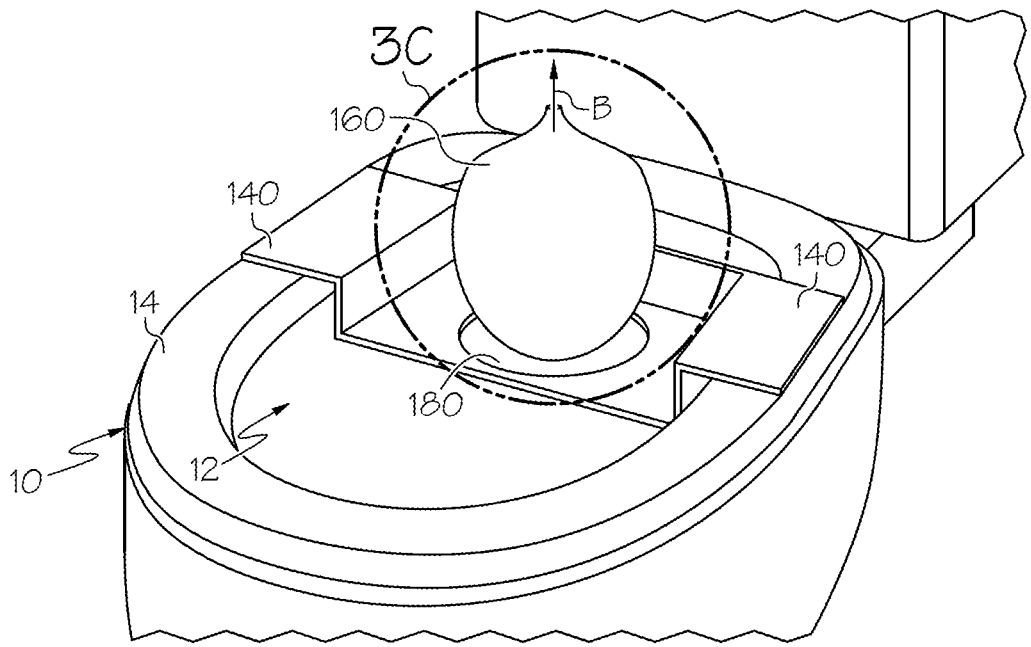
FIG. 3B is a partial perspective view of a sealable carrier received on the sample collection device of FIG. 1, according to aspects of this disclosure.
Figure 3C:
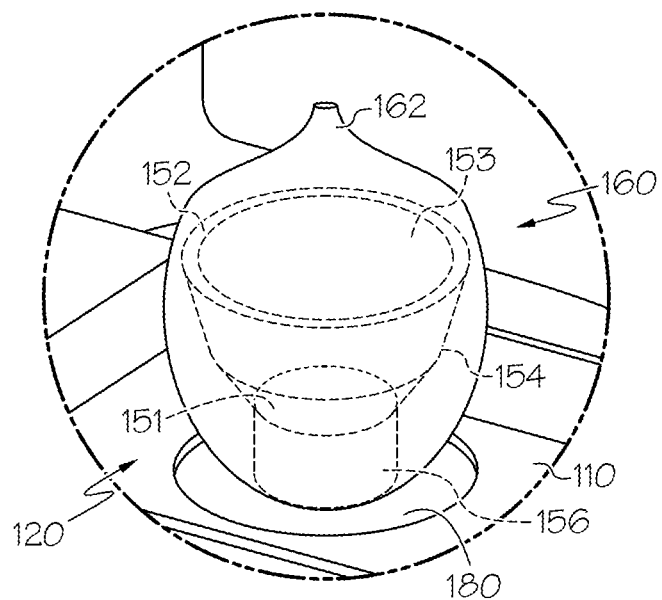
FIG. 3C is a partial perspective view of the sealable carrier disposed over the vessel of FIG. 2, according to aspects of this disclosure.

With the cavity 153 exposed along a top end of the collector vessel 150 adjacent to the top lip 152, the collector vessel 150 may be configured to receive one or more materials (e.g., stool samples) within the bowl portion 154, such as, for example, from a patient using the toilet 10. In this instance, with the material received within the cavity 153, the collector vessel 150 may be enclosed within a sealable carrier 160 of the sample collection device 100, as seen in FIG. 3B. In the embodiment, the sealable carrier 160 is a bag that may be sized and shaped to envelop the collector vessel 150 therein. Accordingly, the bottom surface 151, the top lip 152, the cavity 153, the bowl portion 154, and/or the analysis module 156 of the collector vessel 150 may be disposed within the sealable carrier 160 to seal the material within the cavity 153, as seen in FIG. 3C. The sealable carrier 160 may be selectively sealed (e.g., adhesive, glue, and/or fasteners) at a top end 162 of the sealable carrier 160 to thereby enclose the collector vessel 150 therein and to minimize or inhibit material leakage after sample collection. The collector vessel 150 and the sealable carrier 160 may be disengaged from the toilet platform 120 by moving the collector vessel 150 and the sealable carrier 160 in a direction B, as seen in FIG. 3B.

In some embodiments, the sealable carrier 160 may be preassembled onto the toilet platform 120 prior to positioning the collector vessel 150 into the aperture 180. In this instance, placement of the collector vessel 150 in the aperture 180 may provide for receipt of the collector vessel 150 within the sealable carrier 160 prior to use of the sample collection device 100. It should be appreciated that the sealable carrier 160 may be maintained in an open state with the top end 162 opened for receiving the collector vessel 150 therein such that the sealable carrier 160 may be closed at the top end 162 upon collecting one or more samples within the collector vessel 150. In other embodiments, the sealable carrier 160 may be preassembled onto the collector vessel 150 prior to positioning the collector vessel 150 into the aperture 180 of the toilet platform 120. In this instance, the collector vessel 150 may be positioned within the sealable carrier 160 such that an assembly of the collector vessel 150 and the sealable carrier 160 may be collectively coupled to the toilet platform 120. The sealable carrier 160 may be closed at the top end 162 upon collecting one or more samples within the collector vessel 150. Additionally and/or alternatively, in some embodiments the collector vessel 150 may be configured and operable to self-seal the bowl portion 154 along the top lip 152.

Figure 4:
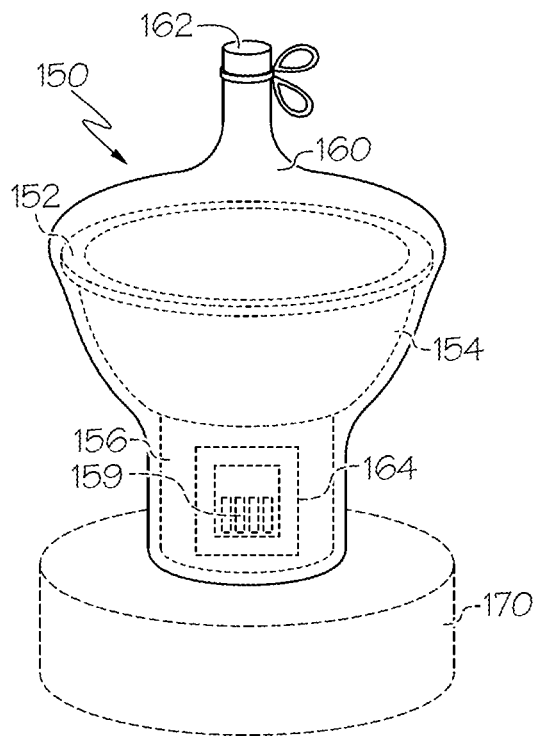
FIG. 4 is a partial perspective view of the vessel of FIG. 2 disposed within the sealable carrier of FIG. 3B and coupled to an exemplary test device, according to aspects of this disclosure.

Referring now to FIG. 4, with the collector vessel 150 enclosed within the sealable carrier 160, an operator of the sample collection device 100 may wait a predetermined duration of time for the analysis module 156 to analyze the material (e.g., stool sample) received within the bowl portion 154. By way of example only, in some embodiments the predetermined duration may range from approximately five minutes to approximately sixty minutes, or approximately ten minutes to approximately fifteen minutes. It should be understood that various predetermined durations for analyzing the material with the analysis module 156 may be suitable without departing from a scope of this disclosure. In this instance, test results from the analysis operation performed by the analysis module 156 may be displayable on the display 159 of the analysis module 156 and/or transmittable to a remote display, mobile device, and/or computer. In embodiments, the sealable carrier 160 may include a transparent window 164 formed thereon, with the transparent window 164 aligned with the display 159 when the collector vessel 150 is received within the sealable carrier 160 to facilitate view of the test results displayed thereon.

In other embodiments, the sample collection device 100 may include a multiple-use cradle 170 that is configured to couple with the collector vessel 150, such as, for example, with the analysis module 156. It should be appreciated that in some embodiments the multiple-use cradle 170 may be communicatively coupled to the analysis module 156 of the collector vessel 150 through the sealable carrier 160. For example, the multiple-use cradle 170 may include a socket disposed along a top surface of the multiple-use cradle 170 that is sized and shaped to receive the collector vessel 150 therein, and more particularly at least a portion of the analysis module 156 of the collector vessel 150. A socket of the multiple-use cradle 170 may include one or more sensors (e.g., an optical sensor, a camera, etc.) configured and operable to detect the analysis module 156 received thereon. By way of further example, the sealable carrier 160 may include a second transparent window positioned along a bottom end of the sealable carrier 160 opposite the top end 162. Accordingly, the second transparent window of the sealable carrier 160 may be alignable with the one or more sensors in a socket of the multiple-use cradle 170 such that the sensor(s) may be configured to detect and communicate with the analysis module 156 through the second transparent window of the sealable carrier 160. In other embodiments, the multiple-use cradle 170 and the analysis module 156 of the collector vessel 150 may be configured and operable to communicate wirelessly with another.

In embodiments, the multiple-use cradle 170 may be operable to analyze the material (e.g., stool sample) received within the cavity 153 of the bowl portion 154 in lieu of and/or in addition to the analysis module 156. Accordingly, the multiple-use cradle 170 may be an external computer system including a non-transitory computer readable medium storing instructions that, when executed by one or more processors of the multiple-use cradle 170, cause the processor(s) to perform the analysis operations described in greater detail above, the results of which may be displayed along the display 159 of the collector vessel 150. In other embodiments, the analysis module 156 and/or the multiple-use cradle 170 may be communicatively coupled to a remote station (e.g., mobile device, computer, etc.) such that the test results of the analysis performed by the sample collection device 100 may transmitted to the remote station. With the collector vessel 150 of the sample collection device 100 sealed within the sealable carrier 160, the collector vessel 150 may be discarded upon completing the analysis of the stool samples.

Figure 5:
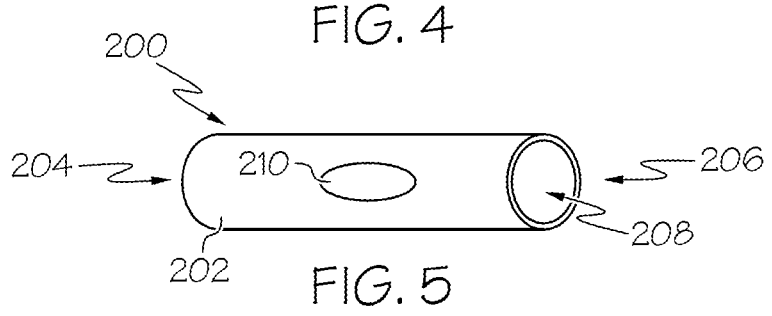
FIG. 5 is a perspective view of another exemplary sample collection device, according to aspects of this disclosure.

Referring now to FIG. 5, another exemplary sample collection device 200 is depicted. The sample collection device 200 includes an elongated body 202 having a distal end 204 and a proximal end 206. The elongated body 202 of the embodiment has a longitudinal length defined between the distal end 204 and the proximal end 206 and forms a substantially cylindrical profile. The elongated body 202 may be formed of various suitable materials, including, but not limited to, metal, composite, plastic, elastomeric material, etc. and may be substantially rigid or flexible. The distal end 204 of the elongated body 202 is closed and the proximal end 206 of the sample collection device 200 includes an opening 208 that facilitates access to an inner channel defined by the elongated body 202. In embodiments, the elongated body 202 is a thimble or a cap that is sized and shaped to receive at least a portion of one bodily feature of an operator through the opening 208, such as, for example, a finger, a plurality of fingers, an appendage, etc. As described in further detail herein, the elongated body 202 is manually maneuverable in response to the elongated body 202 receiving a finger of a user through the opening 208 (see FIGS. 7-9).

The sample collection device 200 further includes one or more adhering portions 210 disposed along the elongated body 202. In embodiments, the one or more adhering portions 210 may be positioned along an exterior surface of the elongated body 202 between the distal end 204 and the proximal end 206. The one or more adhering portions 210 are configured to receive, retain and/or adhere a material thereon, such as, for example, a stool sample of fecal matter from a patient. In some embodiments, the adhering portion(s) 210 is one or more grooves, notches, crevices, cavities, recesses, slots, and/or the like. In this instance, the one or more adhering portions 210 form a depressed surface relative to adjacent portions of an exterior surface of the elongated body 202. As described in greater detail herein, a size, shape, and/or configuration of the adhering portion 210, such as, for example, a volume defined by the at least one groove, notch, crevice, cavity, recess, or slot corresponds to a predetermined volume of material to be received within the adhering portion 210 for adequately analyzing the material (to ensure the volume of material does not exceed an amount suitable to be used with a predetermined volume of substance included in the sample collection device 200 for analyzing the material with improved accuracy). In other embodiments, an outer boundary about the adhering portion 210 may define an area along an exterior surface of the elongated body 202 that a material (e.g., fecal matter) may adhere to.

Figure 6:
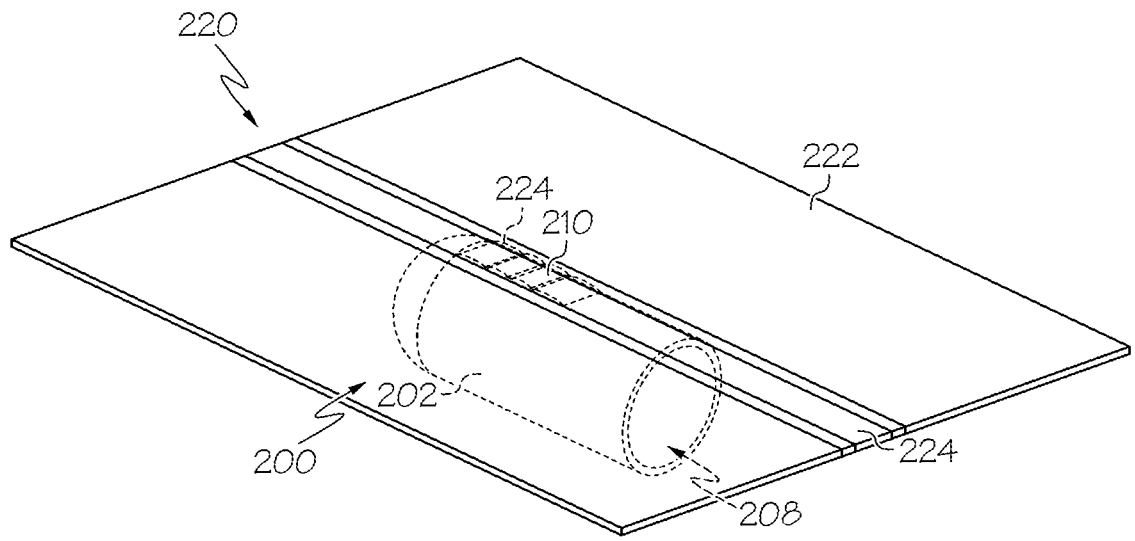
FIG. 6 is a perspective view of the sample collection device of FIG. 5 engaged with a paper, according to aspects of this disclosure.

Referring to FIG. 6, in some embodiments the sample collection device 200 may further include a paper 220 having an outer surface 222 and at least one window opening 224 through the outer surface 222. In the embodiment, the paper 220 is toilet paper and/or tissue paper or other generally absorbable material configured and operable for use by a user to clean the body of fecal material after defecation. It should be understood that the window opening 224 of the paper 220 extends through the outer surface 222 to an inner surface of the paper 220, which is positioned opposite of the outer surface 222. It should be further be appreciated that the outer surface 222 and the inner surface of the paper 220 are not intended to be limiting such that the surfaces of the paper 220 may be interchangeable with one another.

In embodiments, the window opening 224 of the paper 220 is a longitudinal slit that extends along a length of the outer surface 222 and corresponding to a longitudinal axis of the elongated body 202, however, in other embodiments the window opening 224 may have various other sizes, shapes, and/or configurations than those shown and described herein. The paper 220 may be selectively coupled with the elongated body 202 of the sample collection device 200 in response to positioning the elongated body 202 against an interior surface of the paper 220. Further, at least one of the one or more adhering portions 210 on the elongated body 202 may be aligned with the window opening 224 of the paper 220. In this instance, the adhering portion 210 on the elongated body 202 is accessible from the outer surface 222 of the paper 220 through the window opening 224 when the elongated body 202 is disposed relatively underneath the paper 220. Thus, the adhering portion 210 is exposed through the window opening 224 of the paper 220 when the outer surface 222 covers the elongated body 202.

Figure 7A:
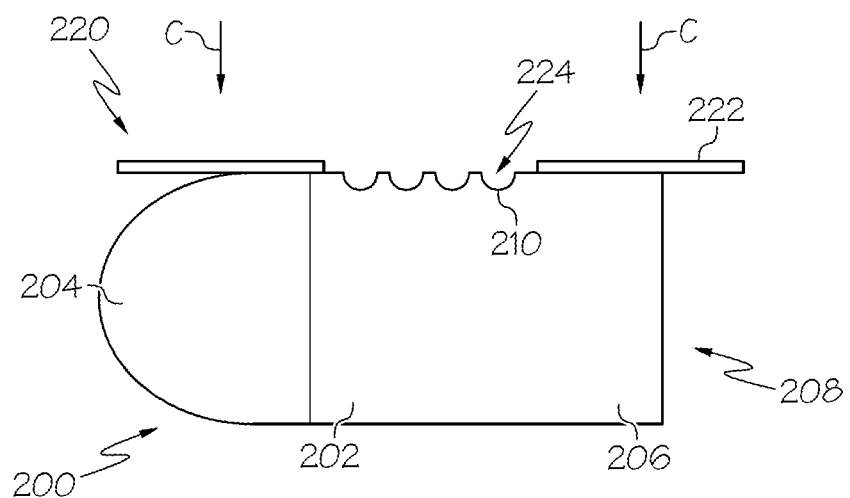
FIG. 7A is a side elevational view of the sample collection device of FIG. 5 engaged with the paper of FIG. 6, according to aspects of this disclosure.

According to an example method of using the sample collection device 200, a user may initially insert a finger through the opening 208 of the elongated body 202 at the proximal end 206. Receiving the finger of the user through an inner channel of the elongated body 202 may allow a user to manually maneuver the elongated body 202 during use of the sample collection device 200. Additionally, in some embodiments, a user of the sample collection device 200 may further couple the paper 220 to the elongated body 202 by moving an interior surface of the paper 220 toward an exterior surface of the elongated body 202 in a direction C as seen in FIG. 7A. It should be understood that in other embodiments an exterior surface of the elongated body 202 may be moved toward the interior surface of the paper 220 to engage the elongated body 202 with the paper 220 without departing from a scope of this disclosure. In either instance, the adhering portion 210 of the elongated body 202 is aligned with the window opening 224 of the paper 220. In the embodiment, the adhering portion 210 of the sample collection device 200 is a plurality of recesses formed along an exterior surface of the elongated body 202. With the elongated body 202 and the paper 220 received on a hand 20 of the user, such as, for example, a finger 22 (see FIG. 2B), a user may utilize the sample collection device 200 to obtain a stool sample.

Figure 7B:
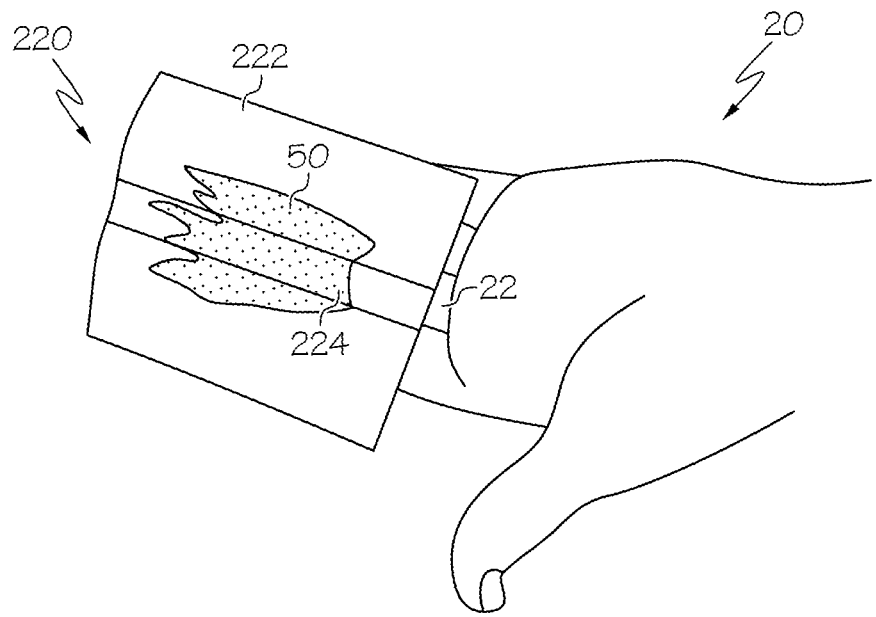
FIG. 7B is a perspective view of the paper of FIG. 6 with fecal matter disposed thereon, according to aspects of this disclosure.

As shown in FIG. 7B, with the sample collection device 200 received along a finger 22 and/or a 20 hand of the user, a user may collect a material 50 along the outer surface 222 of the paper 220 in response to physically contacting the material 50 with the finger 22 and/or the hand 20. In the embodiment, the material 50 is fecal matter dispensed from the user's body such that wiping a region of the user's body containing the material 50 (e.g., rectal area) with the elongated body 202 and the paper 220 positioned along the finger 22 and/or the hand 20 allows for a collection of the material 50 thereon. It should be understood that use of the paper 220 with the elongated body 202 of the sample collection device 200 may be optional such that the paper 220 may be omitted entirely in other embodiments.

Figure 7C:
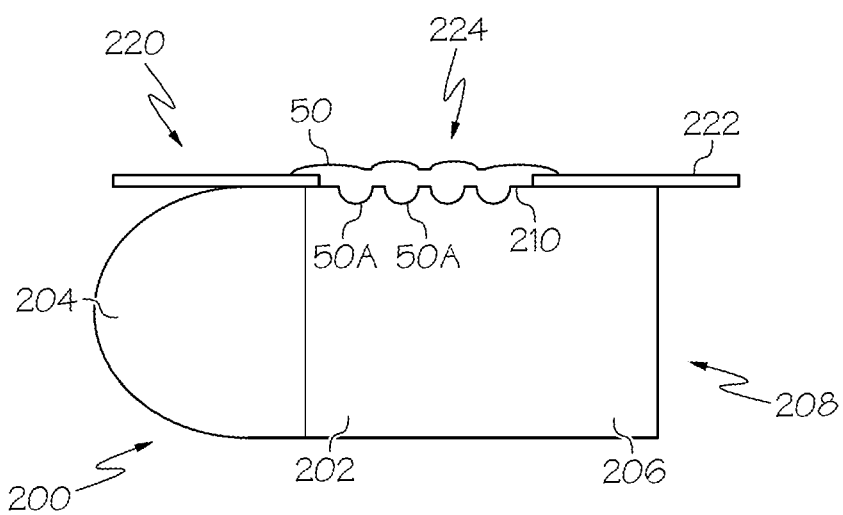
FIG. 7C is a side elevational view of the sample collection device of FIG. 5 engaged with the paper of FIG. 6, the paper including fecal matter disposed thereon, according to aspects of this disclosure.

At least a portion of the fecal matter 50 received along the outer surface 222 may be positioned along the window opening 224 of the paper 220. In this instance, with the elongated body 202 of the sample collection device 200 positioned underneath the paper 220, the adhering portion 210 may receive at least a sample portion 50A of the fecal matter 50 through the window opening 224 of the paper 220, as seen in FIG. 7C. It should be understood that the sample portion 50A adhered to the adhering portion 210 is a relatively minimal quantity of the fecal matter 50 received along the paper 220. In embodiments, with the adhering portion 210 having a plurality of recesses formed along an exterior surface of the elongated body 202, the sample portion 50A of the fecal matter 50 received along the outer surface 222 of the paper 220 may be at least partially deposited within one or more of the plurality of recesses of the adhering portion 210.

Figure 7D:
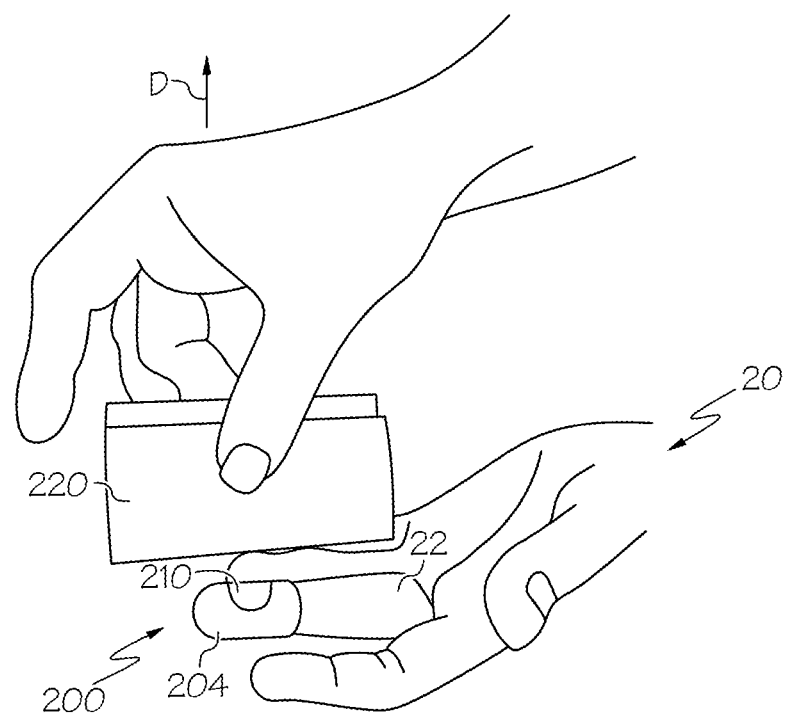
FIG. 7D is a perspective view of the paper of FIG. 6 disengaged from the sample collection device of FIG. 5, according to aspects of this disclosure.
Figure 7E:
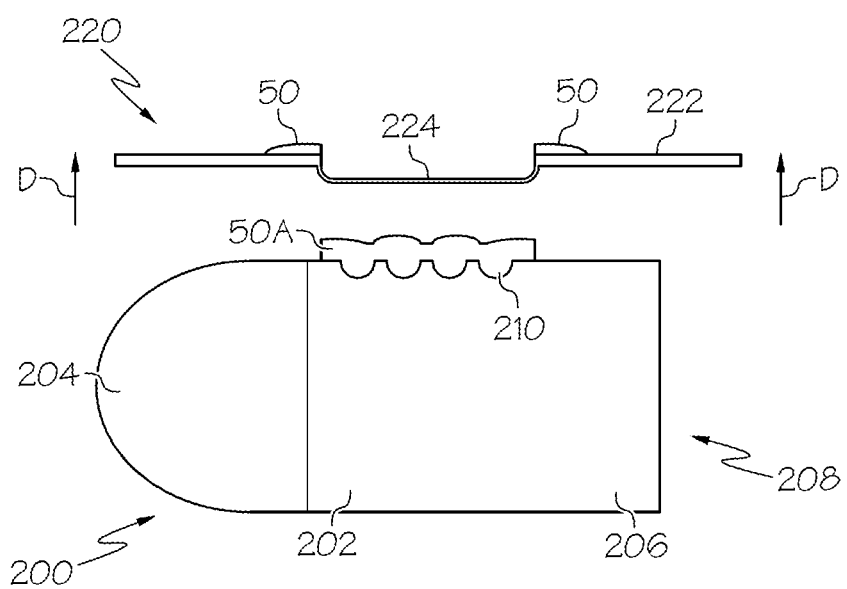
FIG. 7E is a side elevational view of the sample collection device of FIG. 5 disengaged from the paper of FIG. 6, the sample collection device including fecal matter disposed thereon, according to aspects of this disclosure.

Referring now to FIG. 7D, the paper 220 may be removed from engagement with the elongated body 202 of the sample collection device 200 in response to physically grasping and/or moving the paper 220 in a direction D. In response to disengaging the paper 220 from the elongated body 202, portions of the fecal matter 50 disposed along the outer surface 222 of the paper 220 is removed from the elongated body 202. In this instance, as seen in FIG. 7E, only the sample portion 50A of the fecal matter 50 is maintained along the elongated body 202 of the sample collection device 200. It should be understood that in some instances an excess quantity of the fecal matter 50 may be received along the paper 220 such that surplus fecal matter 50 may be received along the adhering portion 210 over the sample portion 50A received in the adhering portion 210. Accordingly, the sample portion 50A of the fecal matter 50 may extend outwardly from the adhering portion 210 relative to an exterior surface of the elongated body 202 as a volume of the fecal matter 50 collected by the sample collection device 200 may be greater than a volume of the adhering portion 210. As described in greater detail below, one or more components of the sample collection device 200 (e.g., a sample test device 230) may be configured to remove the excess volume of the fecal matter 50 from the adhering portion 210 (to ensure the volume of material on the adhering portion 210 does not exceed an amount suitable to be used with a predetermined volume of substance included in the sample test device 230 for analyzing the material with improved accuracy).

Figure 8B:
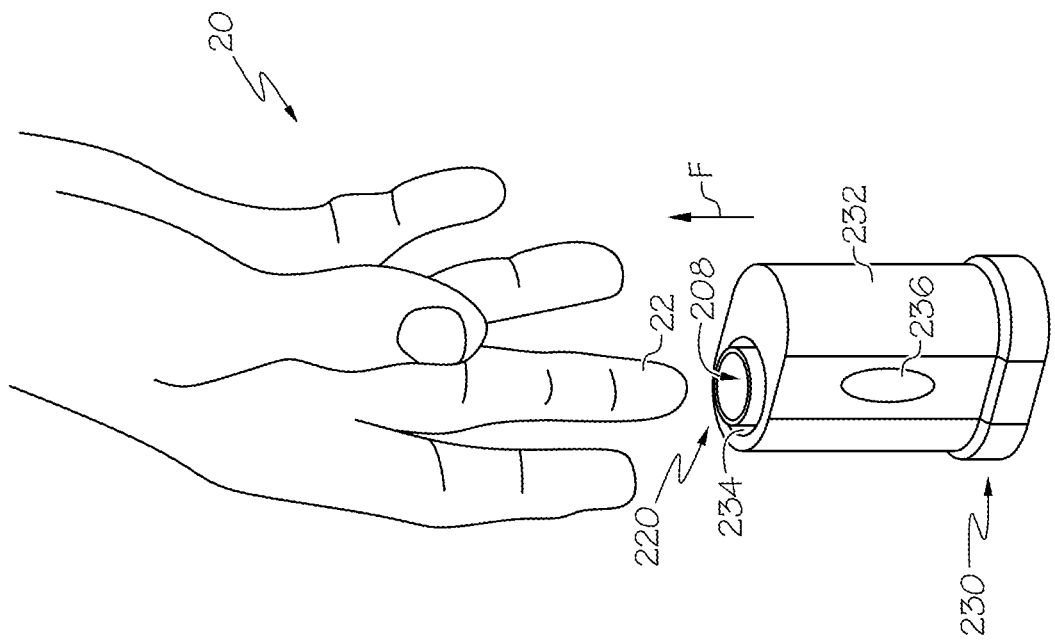
FIG. 8B is a perspective view of the sample collection device of FIG. 5 received within the sample test device of FIG. 8A, according to aspects of this disclosure.
Figure 8A:
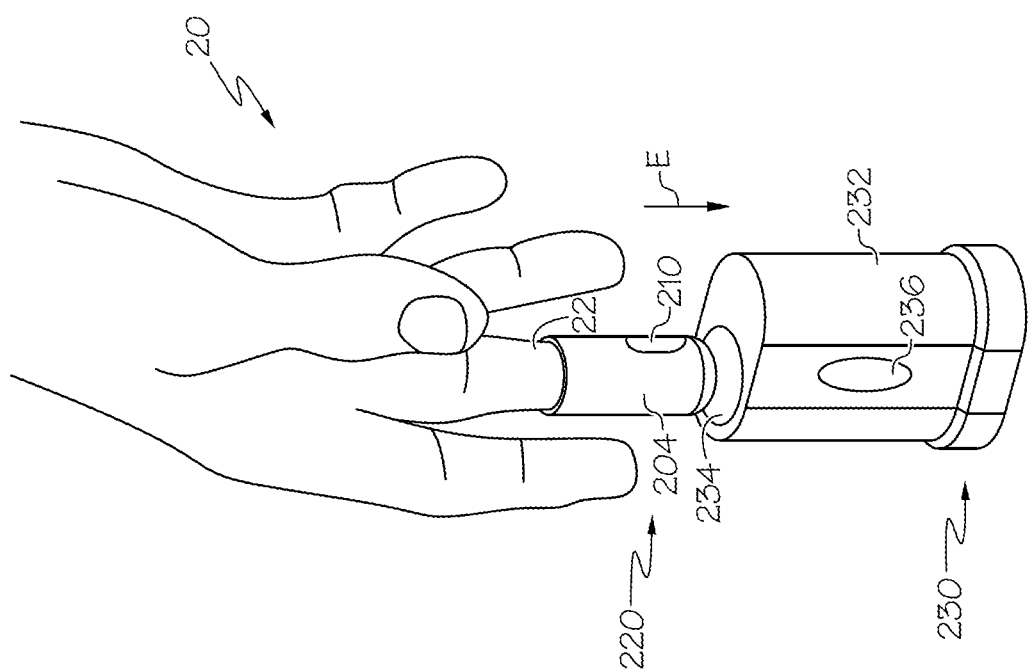
FIG. 8A is a perspective view of the sample collection device of FIG. 5 and an exemplary sample test device, according to aspects of this disclosure.

Referring to FIG. 8A, the elongated body 202 of the sample collection device 200 may be insertable into a sample test device 230 for analyzing the sample portion 50A of the fecal matter 50. The sample test device 230 may include a housing 232, a device opening 234, and an interface display 236. The interface display 236 may be positioned along an exterior surface of the housing 232. The device opening 234 of the sample test device 230 is configured to at least partially or wholly receive the elongated body 202 of the sample collection device 200 therethrough. Accordingly, a user may insert the sample collection device 200 within the housing 232 of the sample test device 230 in response to moving the distal end 204 of the elongated body 202 toward the device opening 234 by physically maneuvering the finger 22 of the hand 20 in a direction E. As described in greater detail below, the opening 234 may be sized to receive the collection device 200 without disturbing the sample portion 50A and to securely capture and/or retain the elongated body 202 within the housing 232 to allow removal of the finger 22 from the sample collection device 200.

It should be understood that the sample test device 230 may be configured and operable similar to the analysis module 156 shown and described above in FIGS. 2-4. For example, the sample test device 230 may be a computer system including a non-transitory computer readable medium and one or more processors, sensors, memory, transceivers, and/or light emitting diodes (LEDs). The non-transitory computer readable medium of the sample test device 230 may store instructions that, when executed by the one or more processors of the sample test device 230, cause the one or more processors to perform certain operations, such as analyzing the sample portion 50A deposited within the adhering portion 210 via one or more sensors in response to the sample test device 230 receiving the sample collection device 200. The interface display 236 is communicatively coupled to the one or more processors of the sample test device 230 such that the interface display 236 is operable to generate a visual display of the analysis results. In other embodiments, the sample test device 230 may be communicatively coupled to a remote station (e.g., mobile device, computer, etc.) such that the test results of the analysis performed by the sample test device 230 may transmitted to the remote station.

Additionally, similar to the analysis module 156, the sample test device 230 may store one or more substances therein for analyzing a material (e.g., stool sample) for the presence of predetermined biomarkers, or bacteria, such as, for example, biomarkers and/or pathogens indicative of Inflammatory Bowel Disease (IBD), Crohn's Disease (CD), Ulcerative Colitis (UC), etc. In embodiments, the analysis module 156 may include substances that are operable to detect the presence of fecal calprotectin within a stool sample, which may be indicative of Inflammatory Bowel Disease (IBD). For example, the one or more substances stored in the sample test device 230 may include monoclonal antibodies operable to determine a qualitative immunoassay for detection of human calprotectin in a material, for detection of one or more IBD biomarkers and/or pathogens.

Referring to FIG. 8B, in some embodiments the sample test device 230 may include one or more retention mechanisms disposed within the housing 232 and/or at the opening 234 for retaining the elongated body 202 of the sample collection device 200 within the sample test device 230 when the finger 22 of the hand 20 is retracted in a direction F. In this instance, a user may be allowed to remove the finger 22 from the inner channel of the elongated body 202 by moving the finger 22 and/or the hand 20 outwardly away from the sample test device 230.

Figure 9:
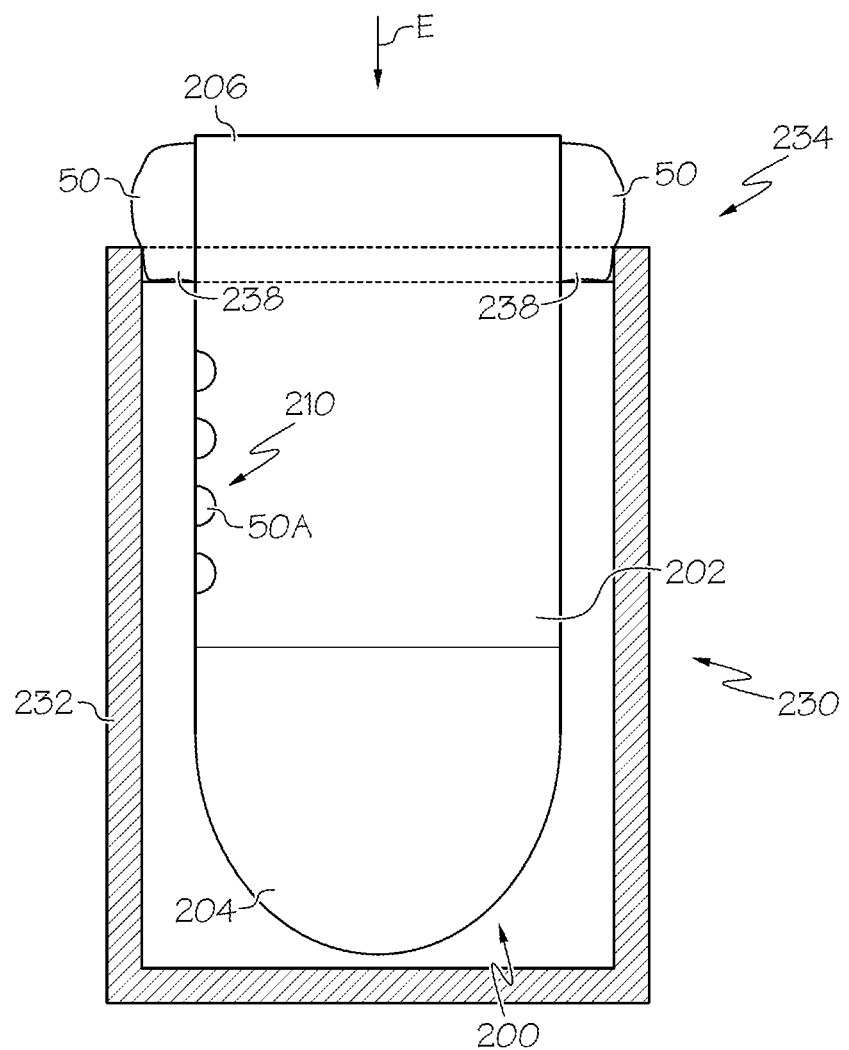
FIG. 9 is a side elevational view of the sample collection device of FIG. 5 received within the sample test device of FIG. 8A, according to aspects of this disclosure.

As shown in FIG. 9, for example, the housing 232 of the sample test device 230 may include a retention mechanism in the form of a seal 238 disposed within the housing 232 adjacent to the opening 234. The seal 238 is an O-ring gasket formed of an elastomer that may be configured to engage an exterior surface of the elongated body 202 in response to the housing 232 of the sample test device 230 receiving the sample collection device 200 therein. The seal 238 may be any mechanism for clamping or locking the sample collection device 200 to the housing 232 such that after insertion of the sample collection device 200 therein the sample collection device 200 remains within the housing 232 when a user retracts a hand in a direction F. Accordingly, the seal 238 is operable to inhibit removal of the sample collection device 200 from the housing 232 of the sample test device 230 upon insertion of the elongated body 202 through the opening 234. It should be understood that the sample test device 230 may include various other suitable retention mechanisms on the housing 232 than those shown and described herein.

Additionally and/or alternatively, the seal 238 of the sample test device 230 may be further configured and operable to remove an excess of the sample portion 50A from the elongated body 202 of the sample collection device 200. As described in greater detail above, in some instances a remaining quantity of the sample portion 50A received along the adhering portion 210 may be in excess of a size of the adhering portion 210 (e.g., a diameter of the plurality of recesses of the adhering portion 210) such that the sample portion 50A may extend outwardly from the adhering portion 210. The seal 238 of the sample test device 230 may be configured to engage the excess fecal matter 50 not received within the adhering portion 210 as the elongated body 202 of the sample collection device 200 is received through the opening 234 of the housing 232 in the direction E. As a result, the excess fecal matter 50 is maintained externally from the housing 232 and only the sample portion 50A received within the adhering portion 210 is positioned within the sample test device 230 (to ensure the volume of material received within the sample test device 230 does not exceed an amount suitable to be used with a predetermined volume of substance included in the sample test device 230 for analyzing the material).

It should be appreciated that the adhering portion 210 (e.g., the plurality of recesses) is sized and shaped to define a predetermined volume that corresponds to a predetermined quantity of the sample material 50A for receipt by the adhering portion 210. The predetermined quantity of the sample material 50A may be determined in accordance with a predetermined quantity of a substance(s) (e.g. liquid) included in the sample test device 230 for diluting the sample material 50A when analyzing the sample material 50A with the sample test device 230. Accordingly, the seal 238 is configured to inhibit the fecal matter 50 received over the adhering portion 210 (in excess of the sample material 50A received within the adhering portion 210) and/or along the elongated body 202 from entering the sample test device 230 when the sample collection device 200 is received therein.

As described above, a size, shape, and/or configuration of the adhering portion 210 corresponds to a predetermined volume of the fecal matter 50 to be received within the adhering portion 210 for adequately analyzing the fecal matter 50 (i.e. the sample portion 50A). Accordingly, the seal 238 of the sample test device 230 is configured to remove the excess fecal matter 50 from the elongated body 202 to thereby maintain the predetermined volume of the sample portion 50A within the adhering portion 210 for analysis by the sample test device 230. Thus, it should be understood that even in instances where physically wiping the bodily region containing the fecal matter 50 (e.g., rectal area) provides excessive collection quantities of the fecal matter 50 on the sample collection device 200 (e.g., in excess of the sample portion 50A), a remaining amount of the fecal matter 50 on the adhering portion 210 after insertion of the elongated body 202 into the sample test device 230 is sufficient for reliable and accurate analysis. An outer boundary of the adhering portion 210 along an exterior surface of the elongated body 202 thereby defines an area in which the excess fecal matter 50 adheres to as the seal 238 engages the fecal matter 50.

In some embodiments, the sample portion 50A received within the sample test device 230 may be passively and/or actively removed from the plurality of recesses of the adhering portion 210. For example, the housing 232 of the sample test device 230 may include a rotating brush, an agitator, and/or a mixer that mixes the sample portion 50A with a liquid. The sample testing device 230 may be further configured and operable to dilute and mix the sample portion 50A received therein with a buffer liquid prior to analyzing the sample portion 50A. Afterwards the sample testing device 230 and the sample collection device 200 may be disposed. With the sample collection device 200 sealed within the sample testing device 230, the sample collection device 200 may be discarded upon completing the analysis of the sample portion 50A.

Referring now to FIGS. 10-14, another exemplary sample test device 330 according to an example of this disclosure is shown. It should be understood that sample collection device 200 may be readily incorporated with sample test device 330 in a similar manner as that described above. It should also be understood that sample test device 330 functions substantially similar to sample test device 230 except for the differences noted herein.

Figure 10:
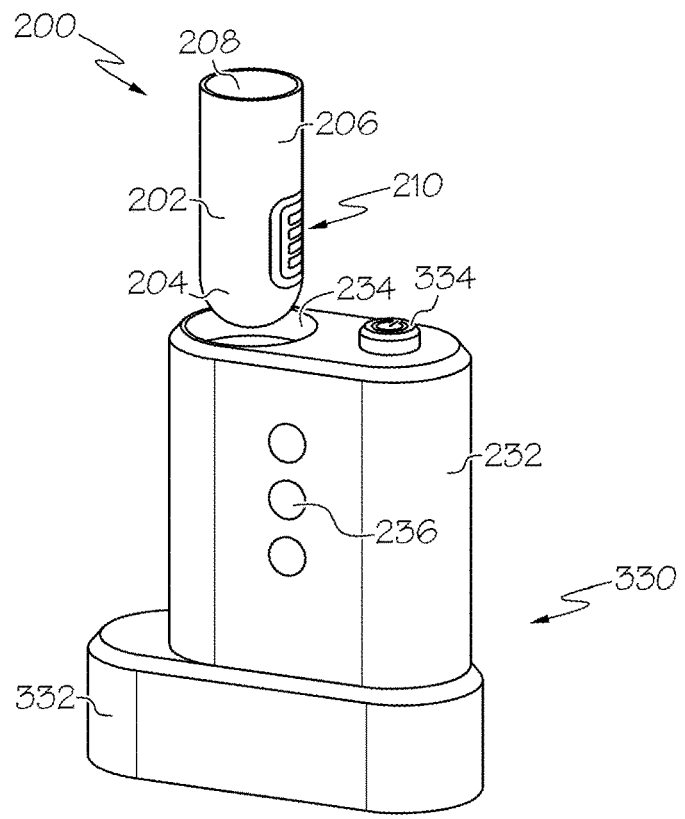
FIG. 10 is a perspective view of another exemplary sample test device and the sample collection device of FIG. 5.

For example, referring initially to FIG. 10, sample test device 330 may include housing 232 with device opening 234 and interface display 236. Sample test device 330 may further include a base 332 secured to a distal end of housing 232, opposite of device opening 234. Base 332 may define a platform of sample test device 330, such that sample test device 330 may be positioned on one or more surfaces along base 332. As described in further detail below, sample test device 330 may include one or more components disposed within a plurality of cavities in housing 232 and/or base 332. Sample test device 330 may further include an actuator 334 along a proximal, top end of housing 232, adjacent to device opening 234. Actuator 334 may include a depressible button configured to actuate one or more components of sample test device 330.

Figure 11:
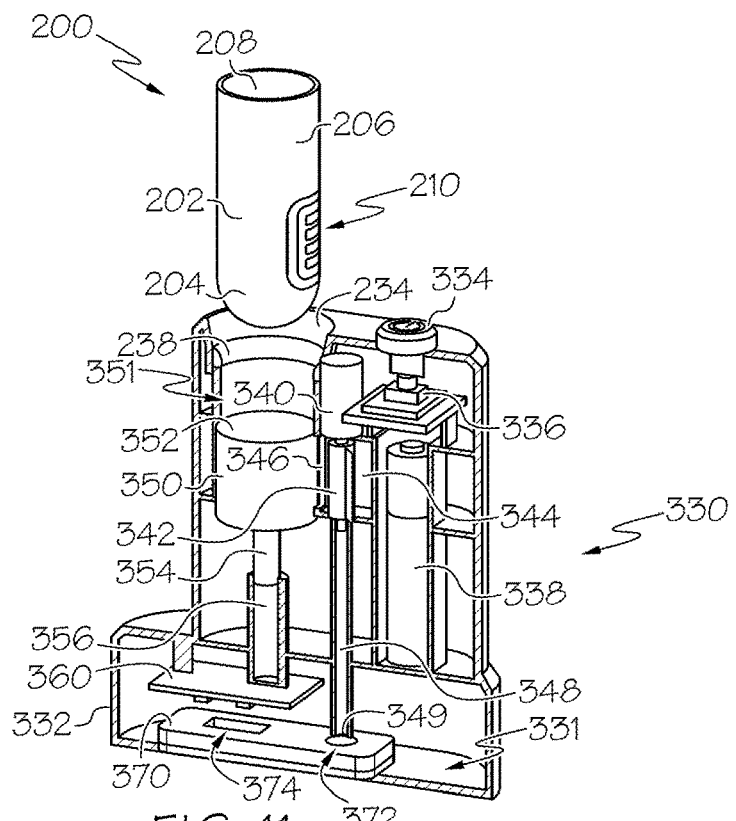
FIG. 11 is a cross-sectional perspective view of the sample collection device of FIG. 5 partially received within the sample test device of FIG. 10.

Referring to FIG. 11, sample test device 330 may include an analysis module 336 disposed within housing 232, which may be operatively coupled to actuator 334 and a power source 338. Analysis module 336 may be substantially similar to analysis module 156 shown and described above. For example, analysis module 336 may include a controller operable to activate a motor 340 of sample test device 330 in response to actuation of actuator 334. Motor 340 may be coupled to a collection device 342, and configured to move (e.g., rotate, translate, etc.) collection device 342 in response to activation of motor 340. In the embodiment, power source 338 may include one or more batteries disposed within housing 232, however, it should be appreciated that power source 338 may include various other electrical energy sources.

In the embodiment, collection device 342 may include a brush having a plurality of bristles extending radially outward from a body of the brush. In other embodiments, collection device 342 may include various other suitable collection and/or cleaning tools. Collection device 342 may be positioned within a chamber 344 of housing 232, and may be configured to move (e.g., rotate, translate, etc.) relative to chamber 344 in response to activation of motor 340. In the example, chamber 344 may store one or more substances for analyzing a material (e.g., a stool sample), such as monoclonal antibodies operable to determine a qualitative immunoassay for detection of human fecal calprotectin. In this instance, collection device 342 may be submerged within the one or more substances stored in chamber 344. As described in further detail herein, chamber 344 may define one of a plurality of cavities of sample test device 330.

Still referring to FIG. 11, sample test device 330 may include an opening 346 along at least one of the internal walls defining chamber 344. For instance, opening 346 may be disposed between a wall separating chamber 344 (e.g., a first cavity) from another cavity (e.g., a second cavity 351) in housing 232. Sample test device 330 may further include a first channel 348 in fluid communication with chamber 344 and another one of the plurality of cavities (e.g. a third cavity 331) in sample test device 330. First channel 348 may have a longitudinal length defined between a proximal end, that is connected to a distal (e.g., bottom) wall of chamber 344, and a distal end 349 disposed within third cavity 331.

In some embodiments, the proximal end of first channel 348 may at least partially extend into chamber 344. Further, at least a portion of collection device 342 may be received within first channel 348 via an opening at the proximal end of first channel 348. Accordingly, collection device 342 may be disposed between motor 340 (e.g., at a proximal, top end of collection device 342) and first channel 348 (e.g., at a distal, bottom end of collection device 342). Collection device 342 may be configured to move (e.g., rotate, translate, etc.) relative to first channel 348 in response to activation of motor 340. First channel 348 may define a lumen and, may be configured to deliver a material (e.g., a sample mixture) received from chamber 344 to base 332 in response to the movement of collection device 342.

Still referring to FIG. 11, sample test device 330 may further include a movable receiver 350 disposed within second cavity 351 of housing 232, defined by device opening 234. Movable receiver 350 may include a body having a proximal interface 352 and a distal interface 354. Proximal interface 352 may be sized, shaped, and configured to receive sample collection device 200 in response to sample test device 330 receiving sample collection device 200 through device opening 234. For example, proximal interface 352 may be sized and/or shaped to have a concave upper surface that corresponds to a configuration of elongated body 202, and particularly distal end 204. In other examples, proximal interface 352 may include an opening, a groove, an indent, and/or other suitable configurations for receiving at least a portion of sample collection device 200.

Distal interface 354 may extend distally from the body of movable receiver 350. In the example, distal interface 354 may have an elongated shape with a cross-sectional profile that is substantially smaller than the body of movable receiver 350. Distal interface 354 may be sized and shaped in accordance with a diameter of a second channel 356 positioned within second cavity 351. In the example, second channel 356 may include a proximal end extending into second cavity 351, and at least a portion of distal interface 354 may be received within second channel 356 via an opening at the proximal end of second channel 356.

Still referring to FIG. 11, second channel 356 may include a longitudinal length defined between the opening at the proximal end, disposed within second cavity 351, and the distal end disposed within third cavity 331. Distal interface 354 of movable receiver 350 may be configured to move (e.g., translate) through second channel 356 in response to sample test device 330 receiving sample collection device 200. Second channel 356 may be configured to control an extent of longitudinal movement by movable receiver 350 within second cavity 351. That is, a longitudinal length of second channel 356 may limit a distance that distal interface 354 may translate as sample collection device 200 pushes proximal interface 352 distally. Second channel 356 may define a lumen having a closed distal end, such that distal interface 354 may be inhibited from exiting second channel 356.

Figure 12:
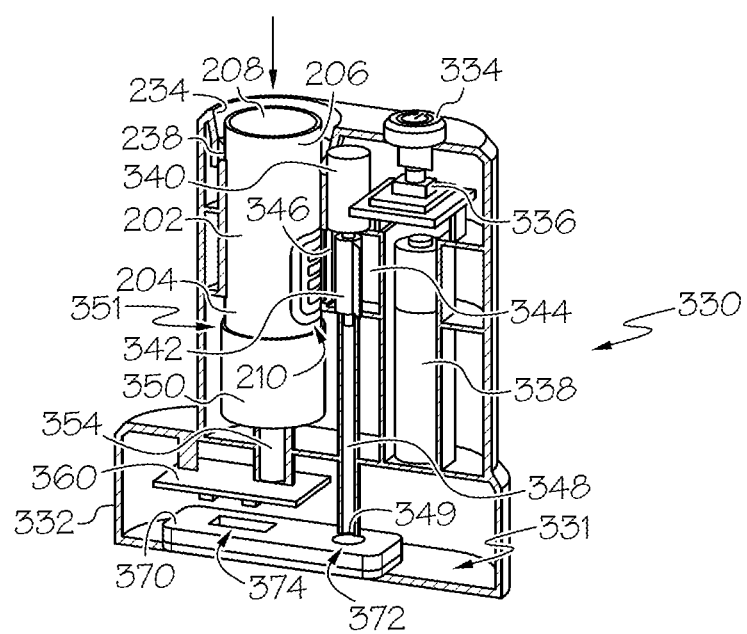
FIG. 12 is a cross-sectional perspective view of the sample collection device of FIG. 5 fully received within the sample test device of FIG. 10.

As seen in FIG. 12, movement of movable receiver 350 may be controlled by the engagement of distal interface 354 with the closed distal end of second channel 356, or by engagement of a distal, bottom face of the body of movable receiver 350 with the proximal end of second channel 356. When in a first, proximal position (see FIG. 11), movable receiver 350 is positioned such that the body of movable receiver 350 overlaps with opening 346. In this instance, the substance stored in chamber 344 may be sealed by the walls of chamber 344 and the body of movable receiver 350. As movable receiver 350 translates distally, movable receiver 350 may be moved to a second, distal position relative to second cavity 351, and elongated body 202 may be positioned against opening 346. Accordingly, the one or more substances may be maintained within chamber 344 despite movement of movable receiver 350. As described in further detail below, upon aligning adhering portion 210 with opening 346, collection device 342 may be configured to extract sample portion 50A from adhering portion 210 and mix sample portion 50A with the substance(s) stored in chamber 344.

Base 332 may include third cavity 331 that is sized and shaped to include a sensing device 360 and a test apparatus 370. In the example, sensing device 360 and test apparatus 370 may be in respective fixed positions relative to third cavity 331, with sensing device 360 positioned overtop test apparatus 370. Test apparatus 370 may include a loading port 372 positioned in alignment with distal end 349 of second channel 348, and a reading window 374 positioned in alignment with sensing device 360. As described in further detail herein, test apparatus 370 may be configured to analyze sample portion 50A obtained by sample collection device 200, and display the test results along reading window 374.

Figure 13:
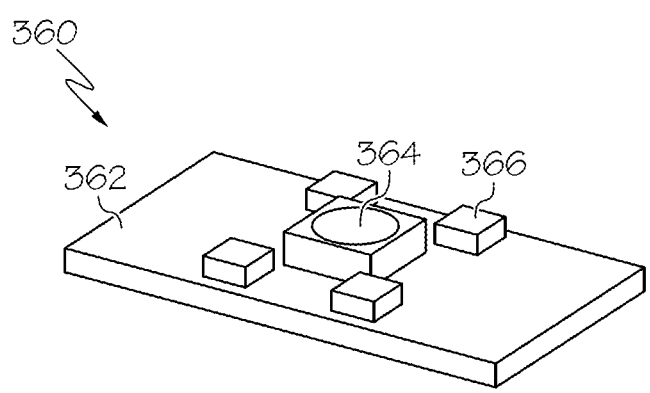
FIG. 13 is a perspective view of a sensing device of the sample test device of FIG. 10.

As seen in FIG. 13, sensing device 360 may include an imaging system (e.g., a camera) having a body 362 having at least one image sensor 364 and at least one optical element 366. Although not shown, it should be appreciated that body 362 may include various electrical circuitry for activating and controlling image sensor 364 and optical element 366. Sensing device 360 may be communicatively coupled to one or more other components of sample test device 330, such as, for example, analysis module 336. In some embodiments, analysis module 336 may be communicatively coupled to imaging device 360 (e.g., via a wired or wireless connection), and configured to activate sensing device 360 upon manual actuation of actuator 334.

In the example, sensing device 360 includes a plurality of optical elements 366 positioned along body 362, and about image sensor 364 in an annular array. Optical elements 366 may provide a light source within third cavity 331 to facilitate visualization of test apparatus 370 by image sensor 364. Stated differently, the plurality of optical elements 366 may be configured to transmit light from sensing device 360 and toward reading window 374. In some embodiments, optical elements 366 may include one or more light-emitting diodes (LEDs). Image sensor 364 may be positioned along body 362 and in between the plurality of optical elements 366. Image sensor 364 may be configured and operable to capture an image (e.g., a digital image) of an object positioned adjacent to sensing device 360, such as test apparatus 370. In some embodiments, image sensor 364 may include a digital sensor. In other embodiments, image sensor 364 may be configured and operable to measure a light intensity of a test line 377 in reading window 374 (see FIG. 14).

Figure 14:
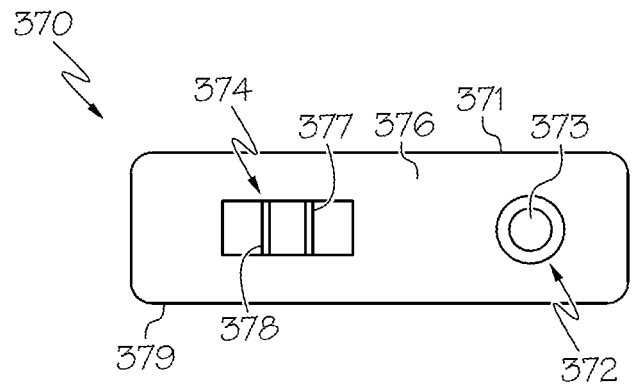
FIG. 14 is a perspective view of a test apparatus of the sample test device of FIG. 10.

Referring to FIG. 14, test apparatus 370 may include a body 376 having a distal portion 371 and a proximal portion 379. Body 376 may be sized and shaped to fit within third cavity 331 of base 332 (see FIGS. 11-12). In other embodiments, as shown and described further herein, test apparatus 370 may include a body 376 that is sized and shaped greater than third cavity 331, such that test apparatus 370 may at least partially extend outward from base 332. Loading port 372 may be positioned along distal portion 371, and reading window 374 may be positioned along proximal portion 379. In the embodiment, test apparatus 370 may include a lateral flow immunochromatographic assay configured to detect the presence of a target substance in a sample after a predetermined duration (e.g., ranging from about 1 minute to about 60 minutes).

Test apparatus 370 may include one or more pads (not shown) disposed within a cavity of body 376, and positioned in series between distal portion 371 and proximal portion 379. For example, each of the one or more pads may be based on a series of capillary beds, such as a porous paper, a microstructured polymer, a sintered polymer, etc. The one or more pads may be configured to receive, absorb, and transport a mixture of sample portion 50A and the substance(s) stored in chamber 344 (e.g., a fluid) received at the distal portion 371, via loading port 372, to the reading window 374 located along the proximal portion 379.

Still referring to FIG. 14, loading port 372 may include a well having an opening 373 that facilitates access to at least one of the pads (e.g., a sample pad) of test apparatus 370. Opening 373 may be sized and shaped to limit a sample volume received through loading port 372. The sample pad at loading port 372 may be configured to receive the sample mixture through the porous material and, once the sample mixture is received, test apparatus 370 may be operable to transfer the mixture (e.g., via fluid flow) to another one of the pads (e.g., an intermediate pad). The intermediate pad may be disposed between loading port 372 and reading window 374, and may include one or more pre-stored particles (e.g., reactive molecules) required for producing a chemical reaction with the sample mixture.

Test apparatus 370 may be further operable to pass the reacted particles and sample through the intermediate pad (e.g., via capillary flow) and to reading window 374, which may include one or more reactive zones. For example, reading window 374 may include at least one test line 377 and at least one control line 378. Test line 377 may be operable to depict a signal, such as in the form of at least one of a plurality of colors and/or at one of a plurality of light intensities. Control line 378 may be operable to indicate whether the sample has effectively flowed through the reading window 374. Additionally and/or alternatively, control line 378 may be operable to facilitate a calibration of sensing device 360 when imaging reading window 374. Test apparatus 370 may include a final pad (e.g., a wick pad; not shown) located distally of reading window 374 for collecting any remaining residue of the sample. In the embodiments, test apparatus 370 may include a competitive assay, a sandwich assay, etc.

According to an example method of using sample test device 330, sample collection device 200 may be inserted into device opening 234 for analyzing the sample portion 50A of fecal matter 50 collected on adhering portion 210 (see FIG. 10). Prior to insertion, movable receiver 350 may be positioned in the first position such that the body of movable receiver 350 closes opening 346 (see FIG. 11). Movable receiver 350 may translate distally relative to second cavity 351 in response to sample collection device 200 abutting against proximal interface 352. As movable receiver 350 is moved to the second position, elongated body 202 may be positioned across opening 346, thereby maintaining chamber 344 in an enclosed, sealed state. It should be appreciated that seal 238 (such as an O-ring) may be configured to generate a frictional resistance against elongated body 202, such that a user may remove a finger from opening 208 without retracting sample collection device 200 from sample test device 330.

Sample collection device 200 may be rotated relative to housing 232 to align adhering portion 210 with opening 346, thereby exposing the sample portion 50A to chamber 344. In some embodiments, elongated body 202 may include a marking (not shown) on proximal end 206 to designate a side of sample collection device 200 which includes adhering portion 210. Further, housing 232 may include a corresponding marking (not shown) on a proximal, top end (e.g., adjacent to device opening 234) to designate a side of sample test device 330 which includes opening 346. In this instance, a user may rotate elongated body 202 relative to housing 232 to align the pair of markings with one another. Actuator 334 may be depressed by a user of sample test device 330 to activate motor 340 and initiate movement of collection device 342. In this instance, collection device 342 may move (e.g., rotate) relative to chamber 344. With adhering portion 210 positioned in alignment with opening 346, collection device 342 may be configured to extend at least partially through opening 346 to contact adhering portion 210. It should be appreciated that, with adhering portion 210 positioned within a separate cavity of housing 232 (e.g., within second cavity 351) than collection device 342 (e.g., within chamber 344), collection device 342 may be configured to at least partially extend into second cavity 351 from the first cavity (chamber 344). For example, the plurality of bristles of collection device 342 may extend into second cavity 351, and contact the adhering portion 210, in response to collection device 342 rotating (e.g., clockwise, counter clockwise, etc.) within chamber 344. In other embodiments, adhering portion 210 may be configured to extend through opening 346 and into chamber 344, to contact the bristles of collection device 342.

Referring to FIG. 12, collection device 342 may be further configured to mix the extracted sample portion 50A with the substance(s) stored in chamber 344. For example, collection device 342 may mix sample portion 50A and substance(s) in response to rotating relative to chamber 344. Collection device 342 may further deliver the sample mixture from the chamber 344 to test apparatus 370 via first channel 348. For example, collection device 342 may be configured to rotate in an opposite direction (e.g., clockwise, counter clockwise, etc.) to transfer the sample mixture through first channel 348. In other embodiments, collection device 342 may translate proximally toward motor 340 to form a gap between proximal end of first channel 348 and a distal end of collection device 342, thereby allowing the sample mixture to move into first channel 348. It should be appreciated that a distal, bottom end of collection device 342 may close a proximal, top end of first channel 348 to maintain chamber 344 in a sealed state until movement (e.g., proximal, upward translation) of collection device 342 allows the sample mixture to transfer through first channel 348.

The sample mixture may be expelled from first channel 348 at distal end 349, and received within test apparatus 370 at loading port 372. The sample mixture may be absorbed and transferred through the one or more pads of test apparatus 370, as described in detail above. Upon generating a graphic visual of the test results on reading window 374, analysis module 336 may activate sensing device 360 to capture an image (or measure a light intensity) of test line 377. Analysis module 336 may initiate display of the test results on interface display 236 (see FIG. 10). Upon reviewing the test results on interface display 236, a user of sample test device 330 may discard sample test device 330 with sample collection device 200 and test apparatus 370 stored therein.

Figure 15:
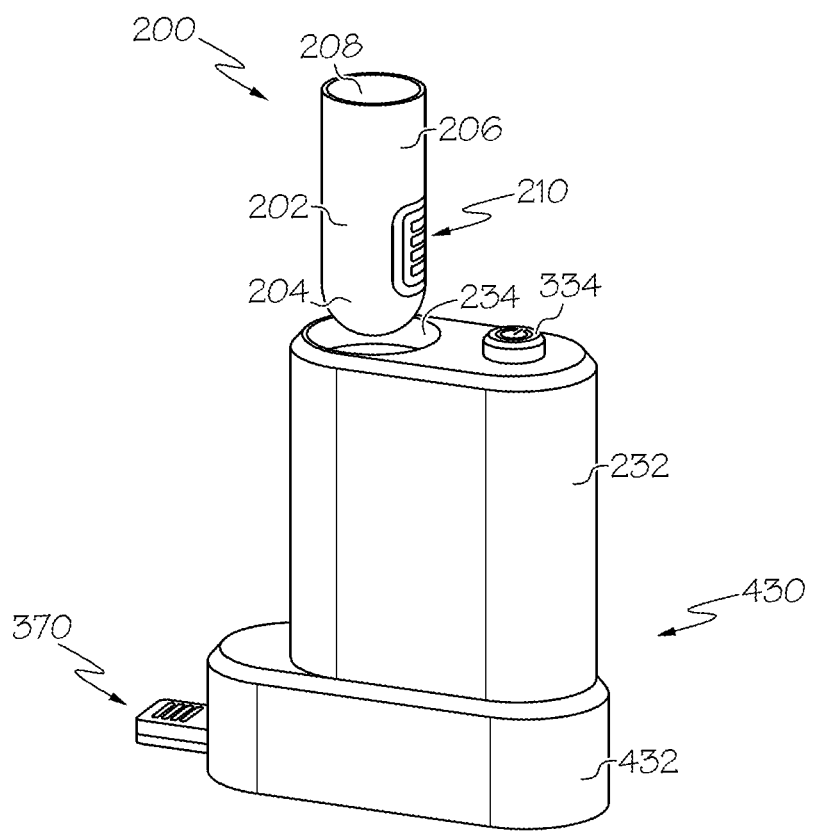
FIG. 15 is a perspective view of another exemplary sample test device and the sample collection device of FIG. 5.
Figure 16:
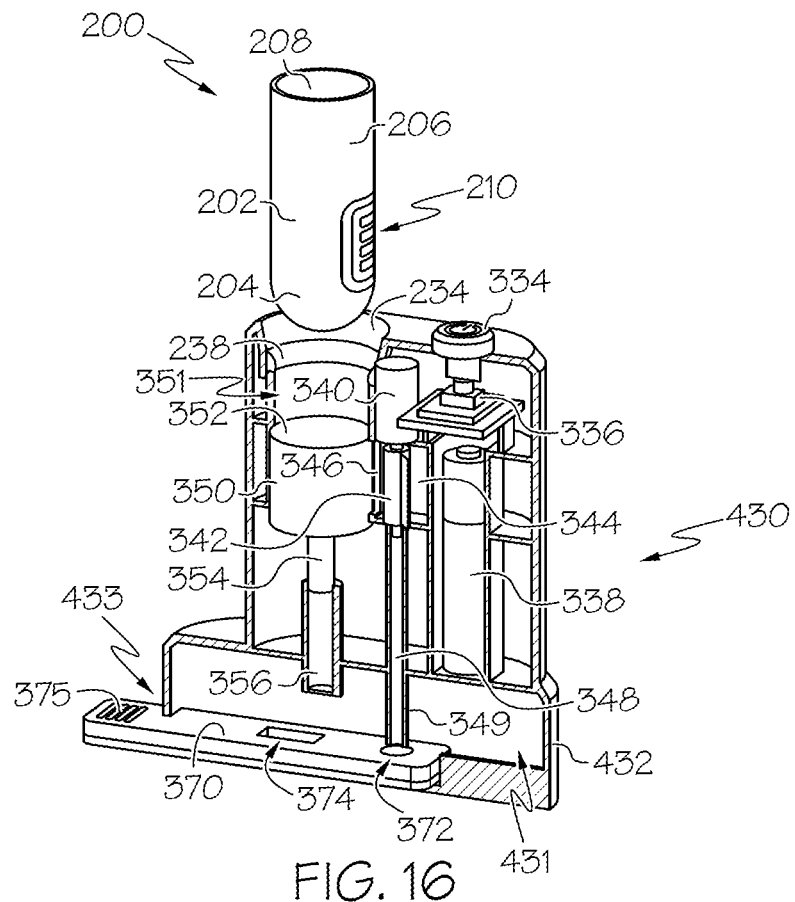
FIG. 16 is a cross-sectional perspective view of the sample collection device of FIG. 5 partially received within the sample test device of FIG. 15.
Figure 17:
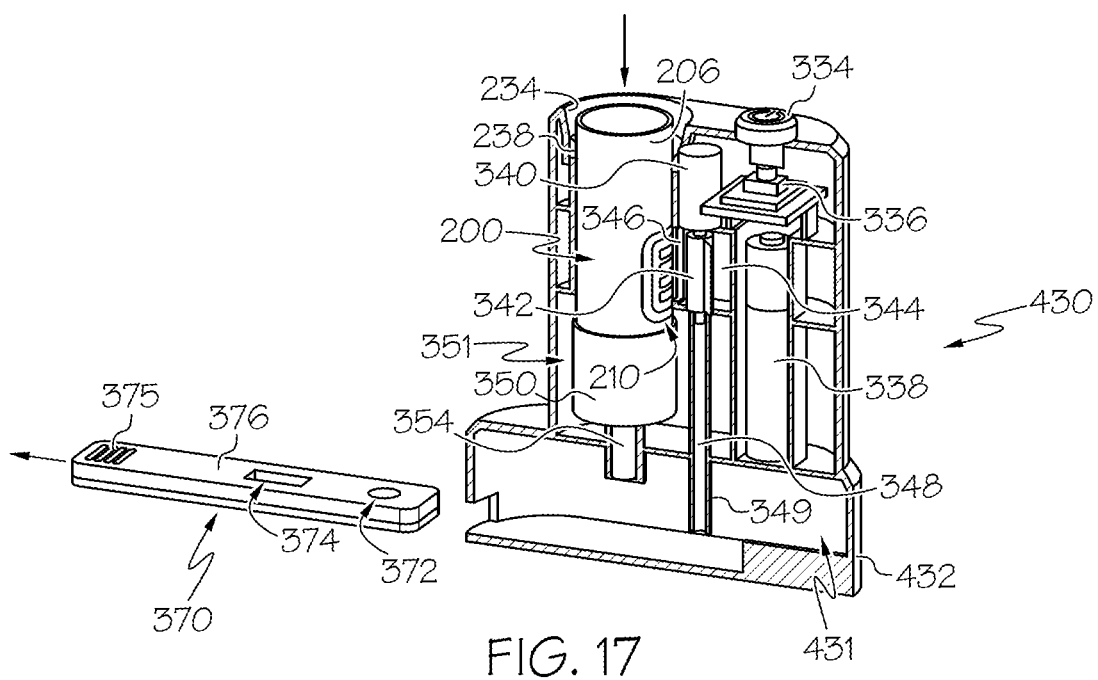
FIG. 17 is a cross-sectional perspective view of the sample collection device of FIG. 5 fully received within the sample test device of FIG. 15.

Referring now to FIGS. 15-17, another exemplary sample test device 430 according to an example of this disclosure is shown. It should be understood that sample collection device 200 may be readily incorporated with sample test device 430 in a manner similar to that described above. It should also be understood that sample test device 430 functions substantially similar to sample test devices 230, 330 except for the differences noted herein. For example, referring initially to FIG. 15, sample test device 330 may include housing 232 and a base 432 secured to a distal end of housing 232. Base 432 may define a platform of sample test device 430, and may be configured to selectively receive test apparatus 370.

Referring now to FIG. 16, base 432 may define a cavity 431 (e.g., a third cavity) that may be accessible via an opening 433 that is sized, shaped, and configured to receive test apparatus 370. Accordingly, test apparatus 370 may be removable from sample test device 430 through opening 433. In the example, test apparatus 370 may include a handle 375 positioned along body 376, opposite of loading port 372. Cavity 431 may be sized such that at least handle 375 is positioned external of base 432 when test apparatus 370 is received within sample test device 430, and particularly when test apparatus 370 is fully inserted, so that a proximal end of test apparatus 370 abuts a wall on flange of base 432. As described in detail herein, test apparatus 370 may be removed from sample test device 430 for analyzing the test results displayed along reading window 374.

In exemplary use, sample test device 430 may be configured to extract sample portion 50A from sample collection device 200 in a manner substantially similar to sample test device 330. For example, movable receiver 350 may be moved from a first position (FIG. 16) to a second position (FIG. 17) upon receiving sample collection device 200 through device opening 234. Collection device 342 may retrieve sample portion 50A from adhering portion 210 upon activation of motor 340 by actuator 334. Sample portion 50A may be mixed with the substance(s) in chamber 344, and transferred to test apparatus 370 in response to movement of collection device 342. Upon receiving the sample mixture at loading port 372, a user of sample test device 430 may remove test apparatus 370 by pulling handle 375 radially outward from base 432.

Figure 18:
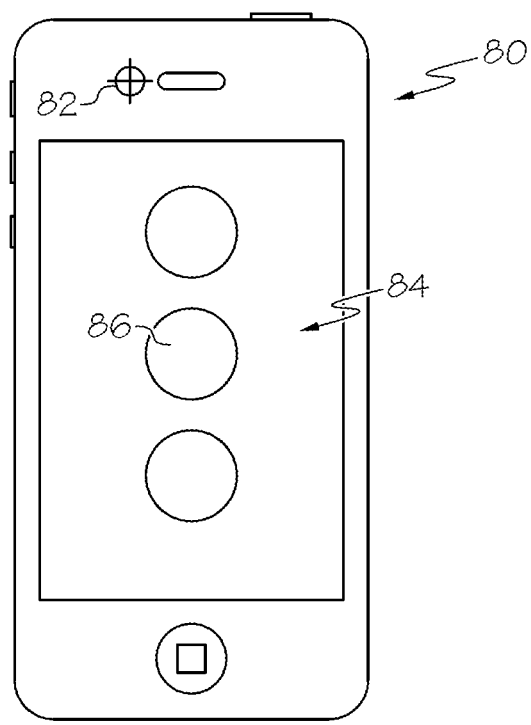
FIG. 18 is a front view of a remote device for use with the sample test device of FIG. 15.

Referring now to FIG. 18, a user may utilize a remote device 80 to capture an image of reading window 374. Remote device 80 may include at least one imaging device 82 and at least one display screen 84. It should be understood that remote device 80 may further include a processor operable to execute a software application stored on a local memory of remote device 80. The software application may include one or more instructions that, when executed by the processor of remote device 80, may provide an analysis of the test results displayed on reading window 374 in a manner similar to that described above with respect to analysis modules 156, 336. In some embodiments, remote device 80 may include a mobile phone, a camera, a computer, and the like. Display screen 84 may generate a graphic visual 86 of the test results analyzed by remote device 80. Upon reviewing the test results on display screen 84, sample collection device 200, test apparatus 370, and sample test device 430 may be discarded. In other embodiments, sample test device 430 may be reusable upon removal of sample collection device 200. Alternatively, a user may view and interpret the test results on reading window 374 without the use of a device (e.g., remote device 80, sensing device 360, etc.).

Figure 19:
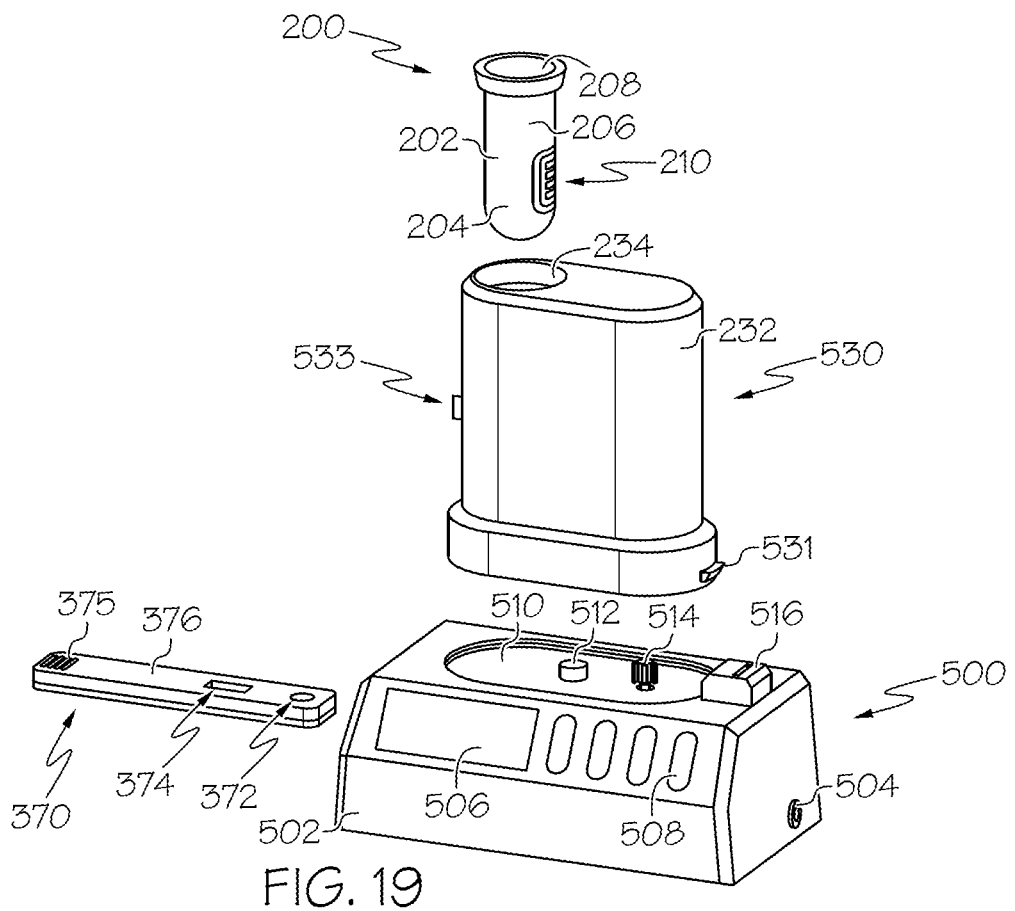
FIG. 19 is a perspective view of another exemplary sample test device including an exemplary docking station, and the sample collection device of FIG. 5.
Figure 20:
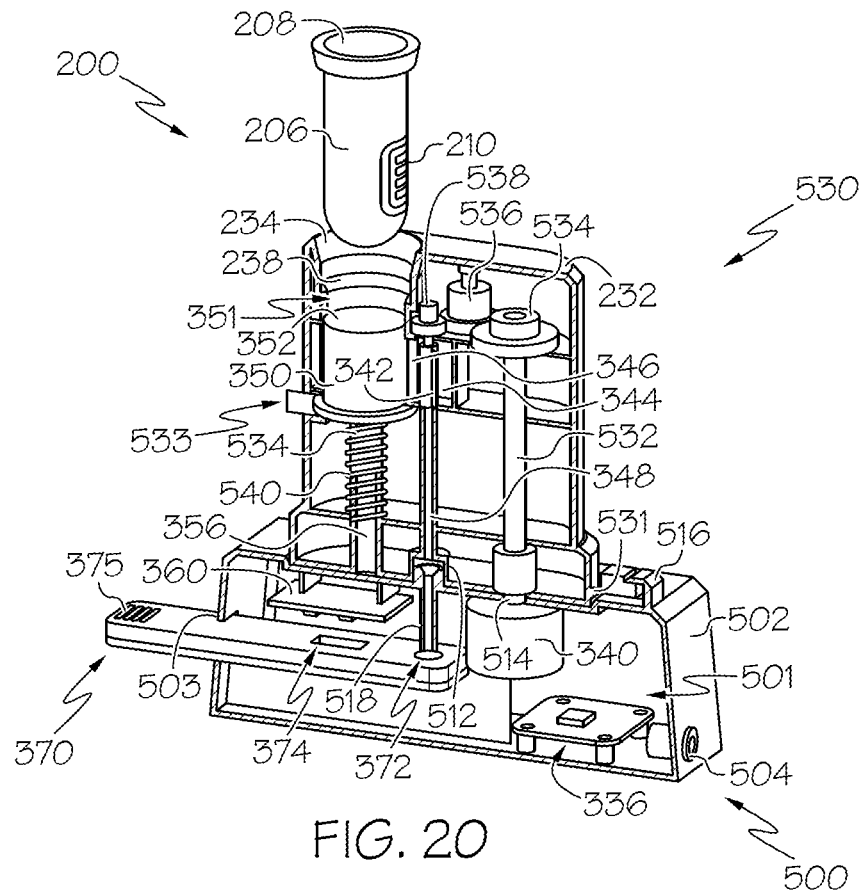
FIG. 20 is a cross-sectional perspective view of the sample collection device of FIG. 5 partially received within the sample test device of FIG. 19, and the sample test device coupled to the docking station.

Referring now to FIGS. 19-20, another exemplary sample test device 530 according to an example of this disclosure is shown. It should be understood that sample collection device 200 may be readily incorporated with sample test device 530 in a manner similar to that described above. It should also be understood that sample test device 530 functions substantially similar to sample test devices 230, 330, 430 except for the differences noted herein.

For example, referring initially to FIG. 19, sample test device 530 may include housing 232 having a first lock assembly 531 and a second lock assembly 533. First lock assembly 531 may include a fixed protrusion extending radially outward from housing 232, and second lock assembly 533 may include a movable protrusion extending radially outward from housing 232. It should be appreciated that lock assemblies 531, 533 may be positioned along various other suitable walls and/or surfaces of housing 232 than those shown and described herein. As described further herein, second lock assembly 533 may be configured to secure sample collection device 200 to sample test device 530, and first lock assembly 531 may be configured to secure sample test device 530 to a docking station 500.

Referring to FIG. 19, docking station 500 may include a housing 502 having at least one port 504, an interface display 506, and/or one or more actuators 508. For example, port 504 may be positioned along a sidewall of housing 502, and may facilitate a connection of one or more components of docking station 510 (e.g., analysis module 336) to an external power source (not shown). Interface display 506 may be operable similar to interface display 236, and actuators 508 may be operable similar to actuator 334. Docking station 500 may include an engagement platform 510 along a top wall of housing 502. Engagement platform 510 may define an interface that is sized and shaped to receive sample test device 530. That is, engagement platform 510 may have a configuration that corresponds to a footprint of housing 232, to facilitate connection between sample test device 530 and docking station 500. Engagement platform 510 may include a sample port 512, a movable pin 514, and a lock assembly 516.

As seen in FIG. 20, sample port 512 may define an opening that facilitates access to a cavity 501 of housing 502. Docking station 500 may include a channel 518 extending distally from sample port 512, and channel 518 may be aligned with loading port 372 when test apparatus 370 is received within docking station 500 (e.g., via opening 503). Movable pin 514 may be coupled to motor 340, and configured to couple motor 340 to a gear assembly of sample test device 530. For example, sample test device 530 may include a gear assembly having a plurality of gears 534, 536, 538 located within housing 232. Each of the plurality of gears 534, 536, 538 may be coupled to one another. In the example, a first gear 534 may be secured to a proximal end of a shaft 532 disposed within housing 232. Shaft 532 may further include a distal end that is positioned opposite of the proximal end, and configured to couple with movable pin 514. Movable pin 514 may be configured to provide a corresponding movement (e.g., rotation) of shaft 532 and first gear 534.

First gear 534 may be positioned within housing 232 adjacent to a second gear 536, and second gear 536 may be positioned adjacent to a third gear 538. Each of the plurality of gears 534, 536, 538 may include a plurality of teeth extending radially outward from a body of the respective gear 534, 536, 538. In the example, first gear 534 may be coupled to second gear 536, and second gear 536 may be coupled to third gear 538, via an engagement of the respective teeth to one another. It should be understood that movement (e.g., rotation) of first gear 534 may provide movement of second gear 536 and third gear 538. In the example, third gear 538 may be coupled to collection device 342, such that movement (e.g., rotation) of third gear 538 may provide a corresponding movement of collection device 342 relative to chamber 344.

Still referring to FIG. 20, lock assembly 516 may be configured to engage first lock assembly 531, to thereby couple docking station 500 to sample test device 530. Lock assembly 516 may include a tab that forms a snap-fit connection with the protrusion of first lock assembly 531. In some embodiments, lock assembly 516 may be selectively actuated to disengage first lock assembly 531, thereby allowing sample test device 530 to decouple from docking station 500. In this instance, sample test device 530 may be removed from docking station 500 and discarded after use. Docking station 500 may further include opening 503 along a sidewall of housing 502. Opening 503 may facilitate access to cavity 501, and may be sized, shaped, and configured to receive test apparatus 370. Docking station 500 may further include analysis module 336 and sensing device 360 disposed within cavity 501.

Sample test device 530 may include a biasing mechanism 540 (e.g., a spring) coupled to movable receiver 350, and particularly along distal interface 356. Biasing mechanism 540 may be configured to apply a proximally-directed (upward) force onto movable receiver 350, thereby biasing movable receiver 350 to the first position (FIG. 20) relative to first cavity 351. Movable receiver 350 may be moved distally to the second position in response to sample collection device 200 applying a distally-directed force that exceeds the proximally-directed force of biasing mechanism 540. In this instance, biasing mechanism 540 may be compressed as movable receiver 350 moves distally within housing 232. Second lock assembly 533 may be at least partially received within first cavity 351. As described further herein, second lock assembly 533 may be configured to lock movable receiver 350 at the second position.

In exemplary use, sample test device 530 may be configured to extract sample portion 50A from sample collection device 200 in a substantially similar manner to sample test devices 330, 430. For example, sample test device 530 may be coupled to docking station 500, and movable receiver 350 may be moved from a first position to a second position upon receiving sample collection device 200 through device opening 234. With movable receiver 350 moved to the second position, and biasing mechanism 340 transitioned to a compressed state, second lock assembly 533 may be actuated (e.g., moved radially inward into housing 232) to fix movable receiver 350 to the second position.

For example, second lock assembly 533 may be pushed into housing 232 by a user. Second lock assembly 533 may be configured to engage an exterior surface of movable receiver 350 and/or sample collection device 200, thereby locking movable receiver 350 to the second position. In other examples, second lock assembly 533 may be received within a corresponding aperture, or positioned against a corresponding ledge and/or tab (not shown), of movable receiver 350 and/or sample collection device 200. Collection device 342 may retrieve sample portion 50A from adhering portion 210 upon activation of motor 340 by at least one of the actuators 508. Sample portion 50A may be mixed with the substance(s) stored in chamber 344, and transferred to docking station 500 via first channel 348 and sample port 512, in response to collection device 342 moving within chamber 344.

Upon receiving the sample mixture through channel 518 and at loading port 372, a user of sample test device 530 may actuate at least one of the actuators 508 to capture an image of reading window 374 with sensing device 360. A user may review the test results generated by test apparatus 370 via interface display 506. It should be understood that docking station 500 may include a processor operable to execute local instructions that provide an analysis of the test results displayed on reading window 374. Upon reviewing the test results on interface display 506, a user may remove test apparatus 370 from docking station 500, and decouple sample test device 530 from docking station 500. Test apparatus 370, sample test device 530, and sample collection device 200 may be discarded, while docking station 500 may be utilized to analyze further test samples after cleaning one or more components of docking station 500 (e.g., channel 518).

Figure 21:
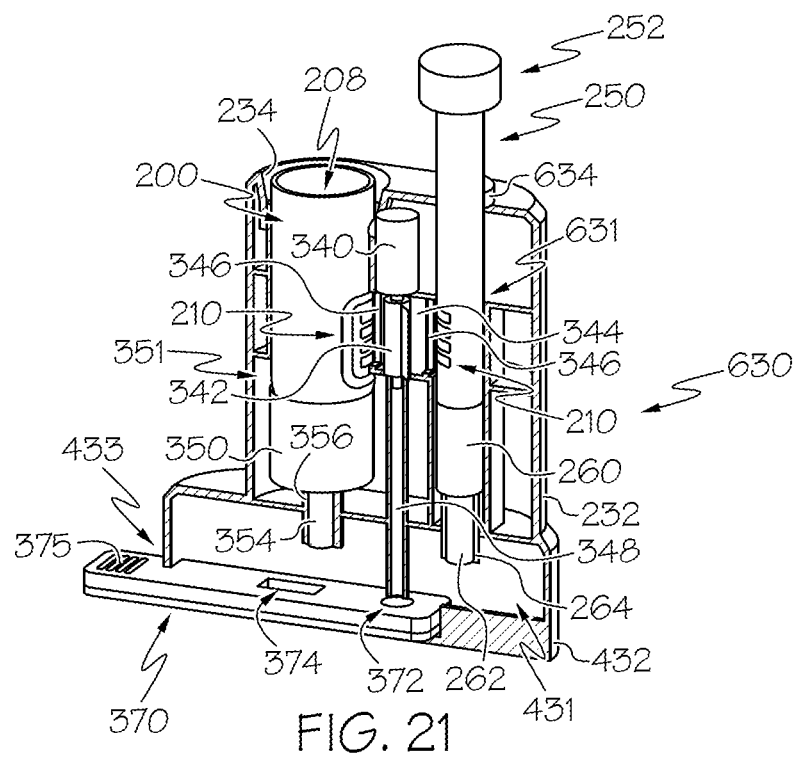
FIG. 21 is a cross-sectional perspective view of another exemplary sample test device including the sample collection device of FIG. 5.

Referring now to FIG. 21, another exemplary sample test device 630 according to an example of this disclosure is shown. It should be understood that sample collection device 200 may be readily incorporated with sample test device 630 in the manner described above. It should also be understood that sample test device 630 functions substantially similar to sample test devices 230, 330, 430, 530 except for the differences explicitly noted herein.

For example, sample test device 630 may include a second device opening 634 positioned along a top wall of housing 232 and that is sized, shaped, and configured to receive another sample collection device 250. Sample collection device 250 may include an elongated body defined by a proximal end 252 and an opposite, distal end. Sample collection device 250 may further include adhering portion 210 positioned along the elongated body, adjacent to the distal end of sample collection device 250.

In the example, proximal end 252 includes a handle and/or knob to facilitate manual control of sample collection device 250. Further, the size and/or shape of the elongated body of sample collection device 250 may vary relative to that of sample collection device 200. In some embodiments, sample collection device 250 may have a smaller cross-sectional profile, and greater longitudinal length, than sample collection device 200. In other embodiments, sample collection device 250 may have a substantially similar profile as sample collection device 200. Sample test device 630 may define a cavity 631 within housing 232 that is aligned with second device opening 634, and configured to receive sample collection device 250.

Cavity 631 may be sized and shaped in accordance with a cross-sectional profile of sample collection device 250. Device opening 234 and second device opening 634, and the corresponding cavities of each, may be offset (separated) from one another by chamber 344 positioned therebetween. Further, housing 232 may include at least one opening 346 positioned between chamber 344 and each of the cavities, such that collection device 342 may be configured to extend into each of the cavities through the respective openings 346. In this instance, sample test device 630 may be configured to extract sample portions 50A from each sample collection devices 200, 250 with the same collection device 342. In other embodiments, sample test device 630 may include a pair of chambers 344 disposed between the cavities of housing 232, and at least one collection device 342 positioned within each chamber 344. In this instance, sample test device 630 may be configured to extract sample portion 50A from each sample collection device 200, 250 with a separate collection device 342.

Still referring to FIG. 21, sample test device 630 may include a (second) movable receiver 260 and a channel 264 disposed within cavity 631. It should be understood that movable receiver 260 may be substantially similar to movable receiver 350. For example, movable receiver 260 may include a proximal interface configured to receive the distal end of second sample collection device 250, and a distal interface 262 extending at least partially into channel 264. Movable receiver 260 may include a size and shape that corresponds with cavity 631, such that movable receiver 260 may have a smaller cross-sectional profile than movable receiver 350.

In other embodiments, sample test device 630 may omit second device opening 634, cavity 631, and movable receiver 260, such that device opening 234 may be operable to receive either sample test devices 200, 250. In this instance, sample test device 630 may further include an adapter (not shown) configured to engage sample collection device 250, and facilitate receipt of sample collection device 250 in device opening 234. For example, the adapter may increase a cross-sectional profile of sample collection device 250 in accordance with a size of second cavity 351. Although not shown, it should be appreciated that sample test device 630 may include one or more further components, including but not limited to, actuator 334, analysis module 336, power source 338, and more.

In further embodiments, sample test device 630 may include a locking mechanism at each device opening 234, 634. The locking mechanism may be configured to inhibit receipt of sample collection devices 200, 250 within the respective device opening 234, 634 when at least one sample collection device 200, 250 is received within housing 232. Stated differently, the locking mechanism may ensure that only one sample collection device 200, 250 is received in sample test device 630 at a time. It should be understood that both sample collection devices 200, 250 are shown in FIG. 21 as simultaneously received within sample test device 630 for illustrative purposes only.

In exemplary use, sample test device 630 may be configured to extract sample portions 50A from sample collection devices 200, 250 in a substantially similar manner to sample test devices 330, 430, 530 described above. In one example, sample collection device 250 may be configured to obtain sample portion 50A by inserting adhering portion 210 into fecal matter 50. A user may manually maneuver sample collection device 250 via the handle at proximal end 252 to direct adhering portion 210 into fecal matter 50 to obtain sample portion 50A. Upon obtaining sample portion 50A with at least one of sample collection devices 200, 250, movable receiver 350 (and/or movable receiver 260) may be moved from a first position to a second position (FIG. 21) upon receiving the corresponding sample collection device 200, 250 through respective device opening 234, 634. Collection device 342 may retrieve sample portion 50A from adhering portion 210 upon activation of motor 340.

In some embodiments, motor 340 may be automatically activated in response to receipt of at least one of sample collection devices 200, 250 within housing 232. In other embodiments, an activation signal may be transmitted to motor 340 by remote device 80 (see FIG. 18). Sample portion 50A from at least one of the sample collection devices 200, 250 may be mixed with the substance(s) stored in chamber 344, and transferred to test apparatus 370 in response to movement of collection device 342. Upon receiving the sample mixture at loading port 372, a user of sample test device 630 may remove test apparatus 370 by pulling handle 375 radially outward from base 432.

Referring to FIG. 18, a user may utilize remote device 80 to capture an image of reading window 374 with imaging device 82. Remote device 80 may analyze the test results displayed on reading window 374, and generate graphical visual 86 of the test results on display screen 84. Upon reviewing the test results on display screen 84, test apparatus 370 may be discarded separately from sample test device 630. In some embodiments, sample test device 630 may analyze at least one sample from each of sample collection devices 200, 250 at a single instance. Accordingly, sample test device 630 may be reusable to analyze additional sample portions 50A upon inserting another test apparatus 370 and sample collection device 200, 250 in housing 232, so long as sample test device 630 does not contain residue in first channel 348, or any residue contained in first channel 348 does not contaminate a subsequent sample analysis. In other embodiments, sample test device 630 may be operable to simultaneously analyze multiple sample portions 50A from both sample collection devices 200, 250.

Each of the aforementioned devices, assemblies, and methods may be used to collect and analyze samples of a material, such as fecal matter from a patient. By providing a sample collection assembly, a user may collect and analyze a sample while maintaining sterility using a sealable apparatus during a procedure, allowing a user to reduce overall procedure time, increase efficiency of procedures, and avoid unnecessary discomfort to a patient's body caused by intrusive devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A sample test device, comprising a housing including a first cavity, a second cavity, and a third cavity;
   at least one opening extending into the first cavity and configured to receive a sample device;
   a motor coupled to a collection device movably disposed within the second cavity and configured to extend into the first cavity to contact the sample device; said collection device is a cleaning and/or mixing movable tool configured to extract a sample portion from an adhering portion of said sample device; and
   a test apparatus disposed within the third cavity, the third cavity is in fluid communication with the second cavity, and the test apparatus is configured to obtain a sample received in the first cavity, via the sample device, in response to activation of said motor which rotates the collection device relative the second cavity.

2. The sample test device of claim 1, further comprising:
   a movable receiver disposed within the first cavity; and
   a second opening positioned between the first cavity and the second cavity;
   wherein the movable receiver is configured to close the second opening when in a first position, and to open the second opening when moved to a second position in response to the first cavity receiving the sample device via the at least one opening.

3. The sample test device of claim 1, wherein the housing includes a channel extending between the second cavity and the third cavity and in fluid communication with a chamber storing one or more substances; and
   wherein rotating the collection device is configured to mix the sample with said one or more substances, resulting in a sample mixture, and deliver the sample mixture via the channel to the test apparatus.

4. The sample test device of claim 1, further comprising a third opening extending into a fourth cavity of the housing and configured to receive a second sample device, wherein the second cavity is positioned between the first cavity and the fourth cavity, and the collection device is configured to extend into the fourth cavity to contact the second sample device.

5. The sample test device of claim 1, wherein said collection device comprises a brush having a plurality of bristles extending radially outward from a body of said brush.

* * * * *